United States Patent [19]

Noire

[11] Patent Number: 5,510,326

[45] Date of Patent: Apr. 23, 1996

[54] MULTI-SUBSTITUTED TETRAHYDROFURANS

[75] Inventor: Paul D. Noire, New York City, N.Y.

[73] Assignee: Givaudan-Roure Corporation, Clifton, N.J.

[21] Appl. No.: 363,685

[22] Filed: Dec. 23, 1994

[51] Int. Cl.⁶ .......................... C07D 307/06; A61K 7/46
[52] U.S. Cl. ............................... 512/11; 512/9; 549/331; 549/356; 549/429
[58] Field of Search .................... 549/429, 331; 512/11

[56] References Cited

U.S. PATENT DOCUMENTS

| | | | |
|---|---|---|---|
| 3,417,107 | 12/1968 | Chodroff et al. | 549/331 |
| 3,463,818 | 8/1969 | Blumenthal | 568/420 |
| 4,404,127 | 9/1983 | Van der Weerdt et al. | 549/429 |
| 4,549,029 | 10/1985 | Hochstetler | 549/429 |

FOREIGN PATENT DOCUMENTS

| | | |
|---|---|---|
| 0266648A2 | 5/1988 | European Pat. Off. |
| 0276998A2 | 8/1988 | European Pat. Off. |
| 1169971 | 7/1985 | U.S.S.R. |

OTHER PUBLICATIONS

Sell, Chem. and Industry, pp. 516–520 (Aug. 20, 1990) "The Chemistry of Ambergris".
Perfumes–Art, Science & Technology, Edited by Muller and Lamparsky, Elsevier Applied Science, pp. 287–296, 324–330, 533, and 547–557.
Fragrance Chemistry—The Science of the Sense of Smell—Ed. by Ernst Thiemer—Academic Press—Chapter 15—The Fragrance of Ambergris, pp. 535–573 (1982).
Ahloff et la., Helvetica Chimica Acta., vol. 69, pp. 163–173, (1986).
Pena et al., Bull. Soc. Chim. Fr. 129, p. 168 (1992).
A. G. Armour, G. Buchi, A. Eschenmoser and A. Storni, Helv. Chim. Acta, 42, No. 240, 2233 (1959).
P. Christenson, B. Willis, F. Wehrli and S. Wehrli, J. Org. Chem., 47, 4786–4789 (1982).
P. Naegeli and Y. Wirz–Habersack, Tetrahedron: Asymmetry, 3, No. 2, 221 (1992).
CA 112:98101n (1989).
M. Stoll and M. Hinder, Helv. Chim. Acta, 33, No. 161, 1251 (1950).
M. Stoll and M. Hinder, Helv. Chim. Acta, 36, No. 246, 1995 (1953).
R. E. Maleczka and L. A. Paquette, J. Org. Chem., 56, 6538–6546 (1991).
M. Stoll and M. Hinder, Helv. Chim. Acta, 38, No. 192, 1593 (1955).
M. Stoll, C. F. Seidel, B, Willhalm and M. Hinder, Helv. Chim. Acta, 39, No. 21, 183 (1956).

*Primary Examiner*—Bernard Dentz
*Attorney, Agent, or Firm*—George M. Gould; George W. Johnston; Mark E. Waddell

[57] ABSTRACT

Novel odorant compositions which are characterized by a content of one or more compounds selected from the group consisting of tetrahydrofurans of structures 1 or 2, or tetrahydropyrans of structure 3.

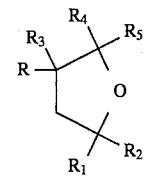

1

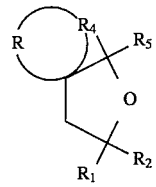

2

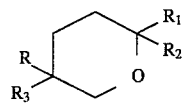

3 wherein R can be an acyclic, where acyclic refers to a chain of at least four carbon atoms substituted with at least three methyl groups in the chain, carbocyclic, where carbocyclic refers to a ring of 5–8 carbon atoms, and with at least two methyl groups on the ring, or bicyclic where bicyclic refers to two carbon rings, each ring having between 5–8 carbon atoms fused together, substituted with at least two methyl groups, and where $R_1=CH_3$, or higher alkyl group, $R_2=H$, $CH_3$, or higher alkyl group, $R_3=H$, or $CH_3$, $R_4$ and $R_5=H$, $CH_3$, or higher alkyl group.

16 Claims, No Drawings

MULTI-SUBSTITUTED TETRAHYDROFURANS

FIELD OF THE INVENTION

The present concerned with novel tetrahydrofurans (THF) of structures 1 or 2, or tetrahydropyrans (THP) of structure 3.

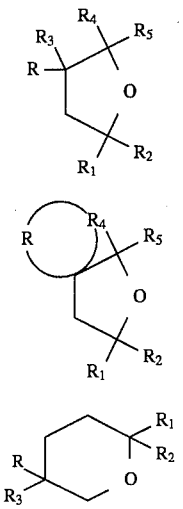

wherein R can be an acyclic, where acyclic refers to a chain of at least four carbon atoms substituted with at least three methyl groups in the chain, carbocyclic, where carbocyclic refers to a ring of 5–8 carbon atoms, and with at least two methyl groups on the ring, or bicyclic where bicyclic refers to two carbon rings, each ring having between 5–8 carbon atoms fused together, substituted with at least two methyl groups, and where $R_1$=$CH_3$, higher alkyl group, $R_2$=H, $CH_3$, or higher alkyl group, $R_3$=H, or $CH_3$, $R_4$ and $R_5$=H, $CH_3$, or higher alkyl group.

The invention is also concerned with their manufacture, odorant compositions which contain said compounds as organoleptic active substances as well as the use of said compounds as odorants.

BACKGROUND ART

THF derivatives with a phenyl group at the C-4 position of the THF ring have been reported in the literature which bear a superficial resemblance to the THF derivatives of this invention. U.S. Pat. No. 4,404,127 describes the preparation of the THF derivatives shown below. Some of these compounds are new. The organoleptic properties of these compounds also are reported. All the THF derivatives claimed in this patent are described as fruity honey like, bloomy, or green. None of these THF derivatives are characterized as amber.

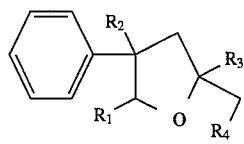

$R_1$, $R_2$, $R_3$ = H, or $C_1$–$C_3$; $R_4$ = H, or $CH_3$, or $C_2H_5$

U.S. Pat. No. 4,549,029 describes the synthesis of novel THF derivatives with a six membered ring at the C-4 position of the THF ring. The substituent at C-4 on the THF ring has no more than seven carbon atoms. These structures are shown below.

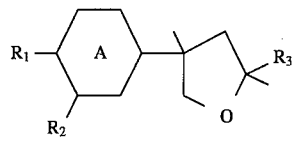

$R_1$, $R_2$, $R_3$ = H or $CH_3$, but $R_1$ and $R_2$ are different
A = benzene, cyclohexadiene, cyclohexene, or cyclohexane Ring These compounds are described as citrus, fruity, floral, or grapefruit. None of these compounds is described as having an amber odor.

C. Sell, Chemistry & Industry, 516 (1990) discusses the chemistry of ambergris including a discussion of newly synthesized amber chemicals. In addition the Chapter entitled "The Fragrance Of Ambergris" by G. Ohloff in Fragrance Chemistry has a discussion of historical aspects related to ambergris, synthesis of amber chemicals, and structural studies. G. Ohloff, Fragrance Chemistry, Ernst Theimer Ed., Academic Press, New York, 1982. Additionally, a discussion of synthetic amber chemicals appears in G. Fráter and D. Lamparsky, Perfumes, Art, Science, & Technology, P. M. Müller and D. Lamparsky Eds. Elsevier Applied Science, New York, 1991, p. 547. A discussion of structure-odor relationships in ambergris odorants appears in the same book by G. Ohloff, B. Winter, and C. Fehr at p. 287.

Ambergris is a secretion of the blue sperm whale. It is found in the intestinal tract of the animal. One of the major components of ambergris is the triterpene ambrein. Ambrein itself is odorless, but as ambrein is broken down outside the whale, the characteristic ambergris odor develops. Some of the compounds responsible for the odor of ambergris are shown below.

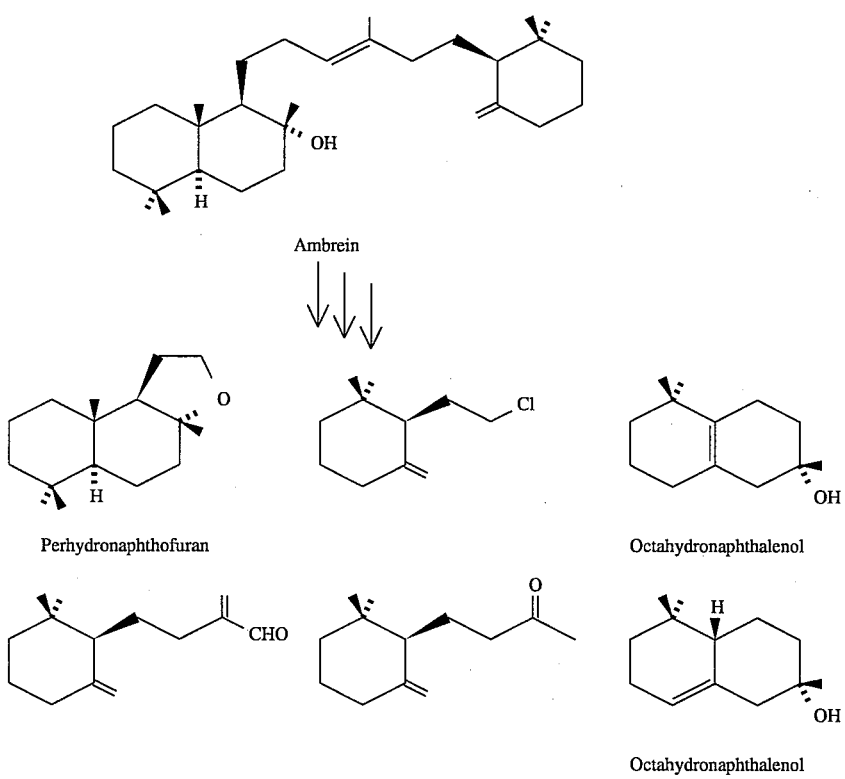

Ambrein

Perhydronaphthofuran

Octahydronaphthalenol

Octahydronaphthalenol

The important components in this mixture are the perhydronaphthofuran and the octahydronaphthalenol. These materials are commercially produced and they are shown below. The perhydronaphthofuntn is known by various tradenames. These include Ambrox®, Ambroxan®, and Amberlyn®.

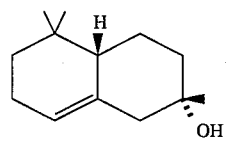

Ambrinol

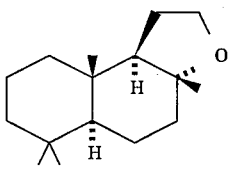

Ambrox

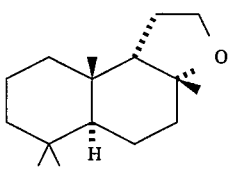

9-Epi-Ambrox

The octahydronaphthalenol is known as Ambrinol®. Ambrox is a highly prized perfume component known for its very free amber odor and fixative properties. It is an expensive perfume chemical. Ambrinol is known for its animal and earthy quality. It is less used but also very expensive.

Ambrox was first synthesized by Stoll and Hinder in 1950. M. Stoll and M. Hinder, Helv. Chim. Acta, 33, 1251 (1950); M. Stoll and M. Hinder, Helv. Chim. Acta, 36, 1995 (1953). More recent syntheses of Ambrox are compiled in G. Fráter and D. Lamparsky, Perfumes, Art, Science, & Technology, P. M. Müller and D. Lamparsky Eds. Elsevier Applied Science, New York, 1991, p. 547. Paquette and Maleczka have recently reported on a highly convergent synthesis of 9-epi-Ambrox and a minor perhydronaphthopyran component found in ambergris. R. E. Maleczka and L. A. Paquette, J. Org. Chem., 56, 6538 (1991).

Commercial syntheses of Ambrox start with the plant clary sage (Salvia sclarea) in which the diterpene sclareol is present. Sclareol is shown below. A degradative pathway involving

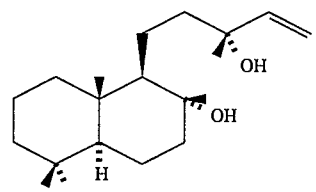

oxidative cleavage, reduction and cyclization has been developed by various workers. L. Ruzicka, C. F. Seidel, and L. L. Engel, Helv. Chim. Acta, 25, 621 (1942); H. R. Schenk, H. Gutmann, O. Jeger, and L. Ruzicka, Helv. Chim. Acta 35, 817 (1952); R. Decorzant, C. Vial, F. Näf, and G. M. Whitesides, Tetrahedron, 43, 1871 (1987); and U.S. Pat. No. 4,798,799.

Ambrinol also has been synthesized by a number of routes. M. Stoll and M. Hinder, Helv. Chim. Acta 38, 1593 (1955); M. Stoll C. F. Seidel, B. Willhalm, and M. Hinder, Helv. Chim. Acta 39, 183 (1956); A. G. Armour, G. Büchi, A. Eschenmoser, and A. Storni, Helv. Chim. Acta 42, 2233 (1959) footnote 8; P. Christenson, B. Willis, F. Wehrli, and S. Wehrli, J. Org. Chem., 47, 4786 (1982); and P. Naegeli and Y. Wirz-Habersack, Tetrahedron Asymmetry, 3,221 (1992). It is the only commercial product available from synthetic starting materials, namely (±)-dihydro-Γ-ionone.

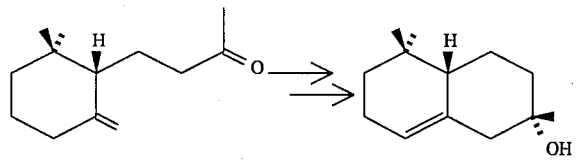

All these previous routes to amber chemicals are expensive. There is a need for cheaper amber chemicals which are more industrially accessible. Vlad reports the preparation of an amber THF derivative shown below. P. F. Vlad, A. F. Morary, and M. N. Koltsa, SU 1169971 (1983) This compound is a C-2,3 disubstituted

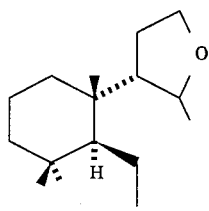

tetrahydrofuran with a substituent at C-3 of the THF ring with eleven carbon atoms. This is substantially different from the compounds claimed in this disclosure.

Sell and coworkers report the preparation and odor properties of some 1,3-dioxane derivatives. EP 276 998 A2. Some of these compounds are shown below. They are completely unrelated to the compounds claimed herein.

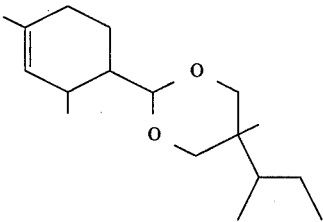

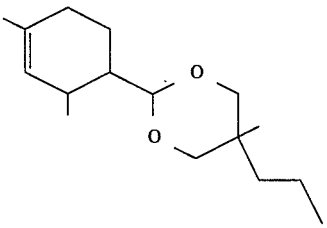

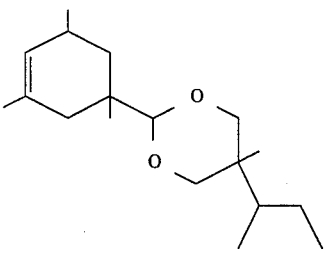

Another series of amber smelling 1,3-dioxanes are reported in EP 266 648 A2. The general structure is shown below. These compounds are not related to the compounds claimed herein.

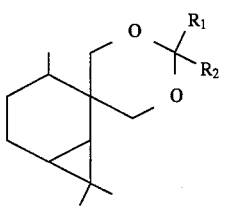

$R_1, R_2 = H, CH_3, C_2H_5, C_3H_7,$ or $CH(CH_3)_2$

Some spirocyclic THF derivatives have been reported to possess an amber odor. Chodroff and Vazirani report the bicyclic compounds shown below are amber in odor characteristic. U.S. Pat. No. 3,417,107. These spirocycles are 3-substituted THF derivatives with no other substituents on the THF ring. They are completely unrelated to the THF derivatives of this invention.

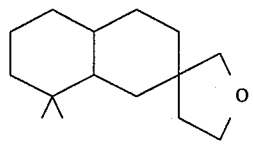

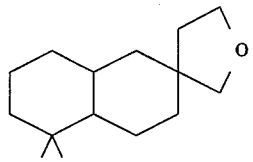

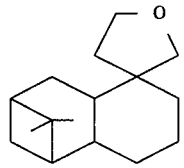

SUMMARY OF THE INVENTION

The invention concerns substituted tetrahydrofurans (THF) and tetrahydropyrans (THP). Many of these compounds have an amber woody odor which is of value in the perfumers' art. These derivatives can be synthesized by the processes outlined in the following schemes.

More particularly, the present invention is concerned with novel odorant compositions which are characterized by a content of tetrahydrofurans (THF) of structures 1 or 2, or tetrahydropyrans of structure 3.

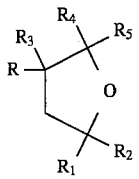

1

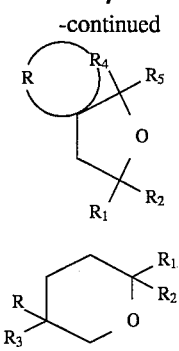

wherein R can be an acyclic, where acyclic refers to a chain of at least four carbon atoms substituted with at least three methyl groups in the chain, carbocyclic, where carbocyclic refers to a ring of 5–8 carbon atoms, and with at least two methyl groups on the ring, or bicyclic where bicyclic refers to two carbon rings, each ring having between 5–8 carbon atoms fused together, substituted with at least two methyl groups, and where $R_1$=$CH_3$, or higher alkyl group, $R_2$=H, $CH_3$, or higher alkyl group, $R_3$=H, or $CH_3$, $R_4$ and $R_5$=H, $CH_3$, or higher alkyl group.

The invention is also concerned with the novel compounds of structures 1–3, their manufacture, odorant compositions which contain said compounds as organoleptic active substances as well as the use of said compounds as odorants.

In the first process (Method 1), a primary or secondary aldehyde (A=H, $CH_3$) is treated with an allylic alcohol, allyl and methallyl alcohol are two examples, in the presence of an acid catalyst. The acetal so formed is treated with citric acid, with or without a solvent and heated in order to crack out one mole of allylic alcohol, thus forming an enol ether which rearranges via the Claisen reaction to α-allylated aldehydes. The so formed α-allylated aldehyde which can be formed as a mixture of diastereomers is treated with a reducing agent to form an alcohol which may be formed as a mixture of diastereomers, which is cyclized with an acid catalyst. The resulting THF or THP derivatives are novel and can be formed as a mixture of diastereomers. These derivatives may possess an unexpected amber-woody odor.

In the second process (Method 2) a primary or secondary aldehyde (A=H, $CH_3$) is treated with an allylic halide under the influence of a strong base in a suitable solvent. The resulting mixture of oxygen and carbon alkylates is heated at 165°–185° C. for an appropriate amount of time until the oxygen alkylate has rearranged via the Claisen reaction to form the C-allylated product. The α-allylated aldehydes may form as a mixture of diastereomers. The so-formed α-allylated aldehyde is now treated as in the first process (Method 1); that is, reduction to the alcohol which may form as a mixture of diastereomers and cyclization with an acid catalyst to the THF or THP derivative. Again these novel THF and THP derivatives may form as a mixture of diastereomers.

METHOD 1

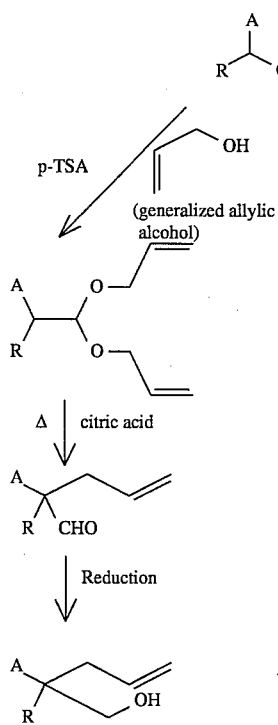

METHOD 2

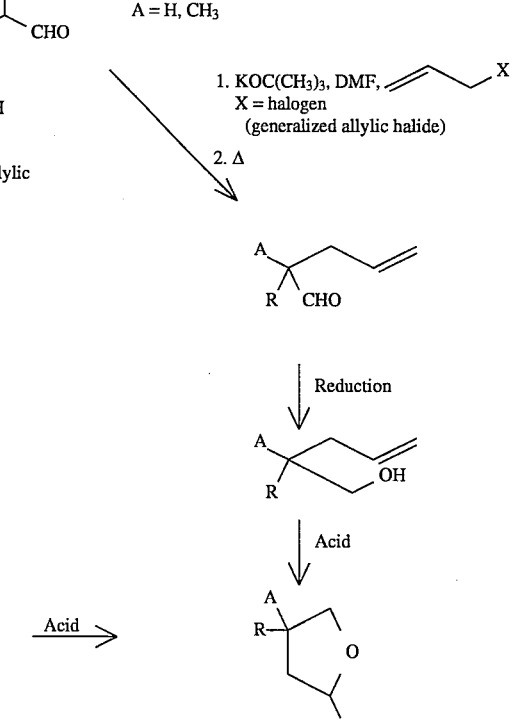

DETAILED DESCRIPTION OF THE INVENTION

The compounds in accordance with the invention comprise tetrahydrofurans (THF) of structures 1 and 2, and tetrahydropyrans of structure 3.

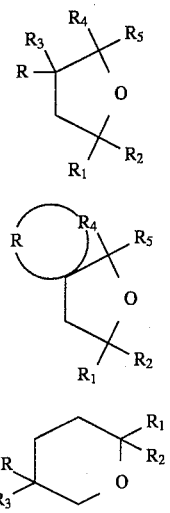

wherein R can be an acyclic, where acyclic refers to a chain of at least four carbon atoms substituted with at least three methyl groups in the chain, carbocyclic, where carbocyclic refers to a ring of 5–8 carbon atoms, and with at least two methyl groups on the ring, or bicyclic where bicyclic refers to two carbon rings, each ring having between 5–8 carbon atoms fused together, substituted with at least two methyl groups, and where $R_1$=$CH_3$ or higher alkyl group, $R_2$=H, $CH_3$, or higher alkyl group, $R_3$=H, or $CH_3$, $R_4$ and $R_5$=H, $CH_3$, or higher alkyl group.

Tetrahydrofurans of structure 2 are representative of spirocycles where R can be carbocyclic, with between 5–8 carbon atoms and at least two methyl groups, or bicyclic with between 5–8 carbon atoms and at least two methyl groups.

By "higher alkyl group" is meant an alkyl group having 2 to 6, preferably 2 to 3, carbon atoms. When substituents $R_1$ to $R_5$ are alkyl, they are most preferably methyl or ethyl.

Some of these compounds with R groups shown in Table 1 are characterized as woody amber. The observation of amber notes is novel and unexpected. The THP derivatives are found to be weaker in odor than the analogous THF derivatives. These compounds are shown in Table 2. Particularly useful are THF compounds where $R_1$=H or $CH_3$ and $R_2$=H or $CH_3$, but $R_1$ and $R_2$ are not both H, and $R_3$=$CH_3$ and $R_4$=$R_5$=H. Also of particular use are spirocycles with R=$C_6$ and a tert-butyl group in the 3 position, and R=bicyclo[4.1.0]heptanyl system with methyl groups at the 7,7,and 11 position.

TABLE 1

| R | $R_1$ | $R_2$ | $R_3$ | $R_4$ | $R_5$ | Odor Description |
|---|---|---|---|---|---|---|
| (cyclopentenyl, dimethyl) | $CH_3$ | $CH_3$ | H | H | H | Amber woody |
| | $CH_3$ | $CH_3$ | $CH_3$ | H | H | Woody Amber |
| | $CH_3$ | $CH_3$ | H | $CH_3$ | H | Amber Woody Animal |
| | $CH_3$ | $CH_3$ | H | $CH_3$ | $CH_3$ | Amber Woody |
| | $CH_3$ | $CH_3$ | $CH_3$ | $CH_3$ | H | Amber Woody Leather Animalic |
| (cyclopentyl, dimethyl) | $CH_3$ | H | H | H | H | Woody Fruity |
| | $CH_3$ | H | H | $CH_3$ | H | Woody Fresh |
| | $CH_3$ | $CH_3$ | H | $CH_3$ | H | Woody Camphoraceous |
| | $CH_3$ | $CH_3$ | $CH_3$ | H | H | Woody Camphoraceous Weak |
| | $CH_3$ | $CH_3$ | H | H | H | Amber Woody |
| (cyclopentenyl, trimethyl) | $CH_3$ | $CH_3$ | H | H | H | Citrus Nootkatone Woody |
| | $CH_3$ | $CH_3$ | H | $CH_3$ | H | Woody Spicy Balsamic |
| | $CH_3$ | $CH_3$ | $CH_3$ | H | H | Woody Cedar Plastic Vanillin Notes |
| (cyclopentyl, trimethyl) | $CH_3$ | $CH_3$ | H | H | H | Amber Woody Labdanum |
| | $CH_3$ | $CH_3$ | H | $CH_3$ | H | Woody Amber Camphoraceous |
| (bicyclic) | $CH_3$ | $CH_3$ | $CH_3$ | H | H | Amber Woody Fruity |

TABLE 1-continued

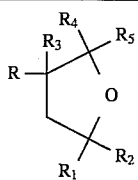

| R | $R_1$ | $R_2$ | $R_3$ | $R_4$ | $R_5$ | Odor Description |
|---|---|---|---|---|---|---|
| (cyclopentyl) | $CH_3$ | $CH_3$ | $CH_3$ | H | H | Woody Fruity |
| (bicyclic) | $CH_3$ | $CH_3$ | H | H | H | Amber Woody |
| | $CH_3$ | H | $CH_3$ | H | H | Woody Amber |
| | $CH_3$ | $CH_3$ | $CH_3$ | H | H | Woody Amber |
| | $CH_3$ | $CH_3$ | H | $CH_3$ | H | Amber Dry Tobacco |
| (bicyclic) | $CH_3$ | H | H | H | H | Woody Amber Weak Fruity |
| | $CH_3$ | H | $CH_3$ | H | H | Woody Powdery Amber |
| | $CH_3$ | $CH_3$ | $CH_3$ | H | H | Woody Sandalwood |
| | $CH_3$ | $CH_3$ | H | H | H | Woody Fruity |
| (cubyl) | $CH_3$ | $CH_3$ | — | H | H | Woody Amber Camphoraceous |
| (branched) | $CH_3$ | H | $CH_3$ | H | H | Fresh Woody Amber Clean |
| | $CH_3$ | $CH_3$ | $CH_3$ | H | H | Decatone Musty |
| (cyclohexenyl) | $CH_3$ | $CH_3$ | H | H | H | Green Rosey Weak |
| (cyclohexyl) | $CH_3$ | $CH_3$ | H | H | H | Bell Pepper Green |
| (bicyclic) | $CH_3$ | $CH_3$ | — | H | H | Timberol Woody Amber |
| (cyclohexyl t-Bu) | $CH_3$ | $CH_3$ | — | H | H | Weak Woody Vetiver |
| | $CH_3$ | H | — | H | H | Fresh Woody Vertinex Cedarwood |

TABLE 2

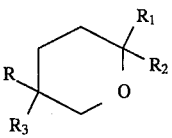

| R | R₁ | R₂ | R₃ | Odor Description |
|---|---|---|---|---|
| 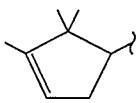 | CH₃ | CH₃ | H | Weak Woody |
| | CH₃ | CH₃ | CH₃ | Fresh Spicey Ginger Milkey Green Nootkatone |
| 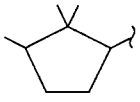 | CH₃ | CH₃ | H | Weak Woody |
| 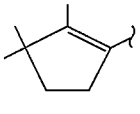 | CH₃ | CH₃ | H | Weak Woody |
| 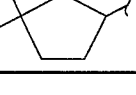 | CH₃ | CH₃ | H | Weak Woody |

Having regard to their valuable olfactory properties with a very broad spectrum, the compounds of the invention are suitable as odorants, especially in combination with the extensive range of natural and synthetic odorants which are nowadays available for the creation of perfume compositions which can be used in all spheres of application. Examples of the numerous known odorant ingredient of natural or synthetic origin, whereby the range of the natural raw substances can embrace not only readily volatile but also moderately volatile and difficultly volatile components and that of the synthetics can embrace representatives from several classes of substances, are:

Natural products, such as tree moss absolute, basil oil, tropical fruit oils (such as bergamot oil, mandarin oil, etc.), mastix absolute, myrtle oil, palmarosa oil, patchouli oil, petit grain oil, wormwood oil, lavender oil, rose oil, jasmine oil, ylang-ylang oil, sandalwood oil, alcohols, such as famesol, geraniol, linalool, nerol, phenylethyl alcohol, rhodinol, cinnamic alcohol, cis-3-hexenol, menthol, α-tocopherol, aldehydes, such as citral, α-hexylcinnaldehyde, hydroxycitronellal, Lilial" (p-tert.butyl-α-methyl-dihydrocinnamaldehyde), methylnonylacetaldehyde, phenylacetaldehyde, anisaldehyde, vanillin, ketones, such as allylionone, α-ionone, β-ionone, isoraldein (isomethyl-α-ionone), verbenone, nootkaton, geranylacetone, esters, such as allyl phenoxyacetate, benzyl salicylate, cinnamyl propionate, citronelly acetate, decyl acetate, dimethylbenzylcarbinyl acetate, ethyl acetoacetate, ethyl acetylacetate, cis-3-hexenyl isobutyrate, linalyl acetate, methyl dihydrojasmonate, styrallyl acetate, vetiveryl acetate, benzyl acetate, cis-3-hexenyl salicylate, geranyl acetate, etc., lactones, such as γ-undecalactone, δ-decalactone, pentadecan-15-olid, various components often used in perfumery, such as indole, p-menthane-8-thiol-3-one, methyleugenol, eugenol, anethol.

In their use as odorants the compounds of the invention (or their mixtures) can be employed in wide limits which in compositions can extend, for example, from about 0.1 (detergents) to about 30 weight percent (alcoholic solutions) without these values being, however, limiting values, since the experienced perfumer can also achieve effects with even lower concentrations or can synthesize novel complexes with even higher dosages. The preferred concentrations vary between about 0.5 and about 10 weight percent. The compositions manufactured with the compounds of the invention can be used for all kinds of perfumed consumer goods (eau de Cologne, eau de toilette, extracts, lotions, creams, body oils, shampoos, soaps, cleansers, air fresheners, salves, powders, toothpastes, mouth washes, deodorants, detergents, fabric conditioners, tobacco, etc.).

The compounds of the invention can accordingly be used in the manufacture of compositions and—as will be evident from the above compilation—a wide range of known odorants or odorant mixtures can be used. In the manufacture of such compositions the known odorants or odorant mixtures enumerated above can be used in a manner known to the perfumer, as follows e.g. from W. A. Poucher, Perfumes, Cosmetics and Soaps 2, 7th edition, Chapman and Hall, London, 1974.

By virtue of their superior olfactory properties the compounds of the invention are preferably used in luxury perfumery and in compositions for cosmetics.

The THF derivatives of this invention are available by two different processes. These two processes are known as method 1 and method 2 and are shown in the figure below.

METHOD 1                    METHOD 2

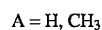

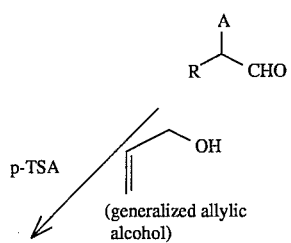

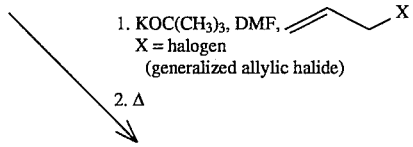

A = H, CH₃

1. KOC(CH₃)₃, DMF, X = halogen (generalized allylic halide)

2. Δ p-TSA (generalized allylic alcohol)

-continued

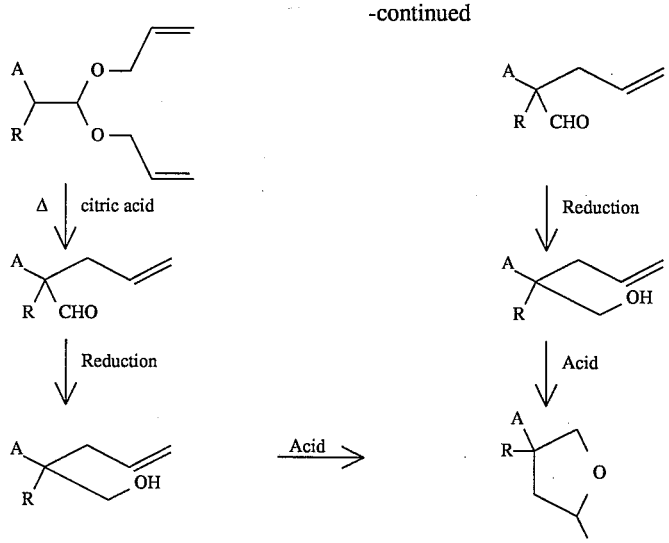

In both processes a primary or secondary aldehyde can be used as the starting material. These aldehydes, where R can be defined as the structures below which in no way limits the choice of the aldehyde, and where A can be defined as a hydrogen atom, or methyl group, are synthesized by well known methods found in the chemical literature and known to those who practice the art. The arrow indicates the position of attachment of the carboxaldehyde group. For example, where R=2,2,3-trimethyl-3-cyclopenten-1-yl and A=CH₃, the synthesis would proceed from 2,2,3-trimethyl-3-cyclopenten-1-yl acetaldehyde (campholenic aldehyde). The first step is hydroxymethylation-dehydration. A representative procedure is described by Schulte-Elte et al. in U.S. Pat. No. 4,610,813. The synthesis is shown in the following diagram.

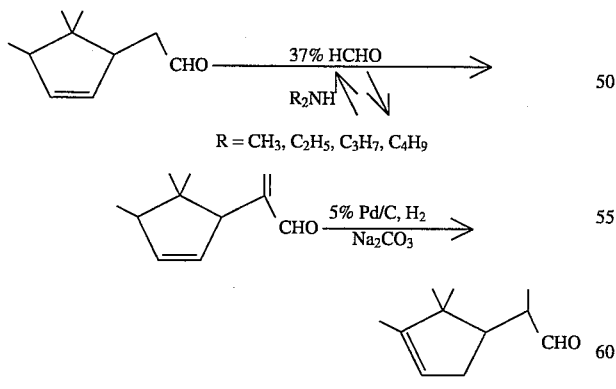

R = CH₃, C₂H₅, C₃H₇, C₄H₉

The second step in the synthesis involves hydrogenation using an appropriate catalyst. A representative procedure for this particular reaction and compound is found in EP 0155591 A2.

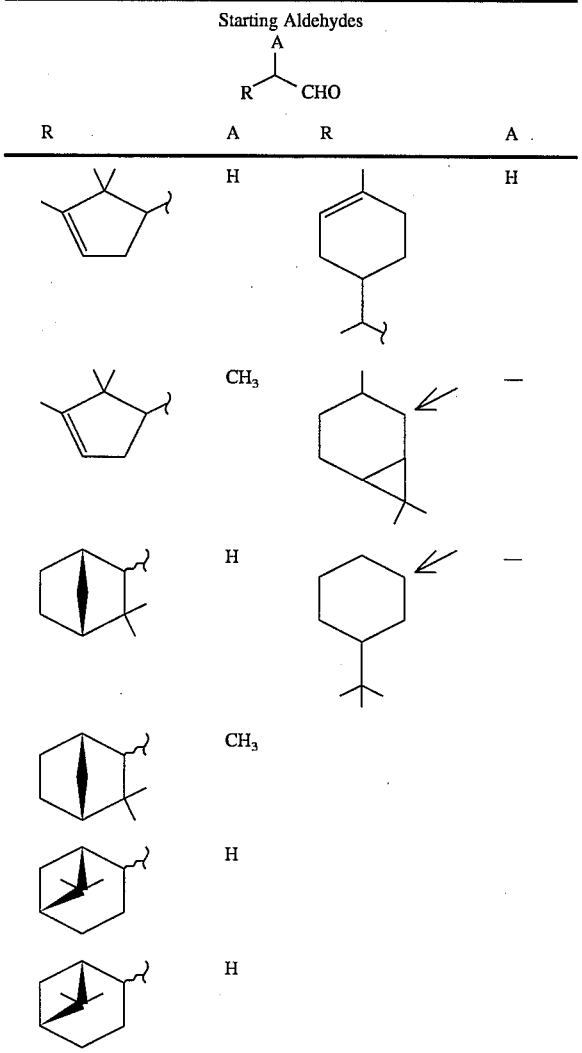

Starting Aldehydes $$R\underset{A}{\overset{A}{-}}CHO$$

| R | A | R | A |
|---|---|---|---|
| (cyclohexene structure) | — | | |
| (isobutyl structure) | H | | |
| (isobutyl structure) | CH$_3$ | | |

In method 1, the aforementioned aldehydes are treated with 2.2–3 equivalents of an allylic alcohol, preferably methallyl or allyl alcohol under the influence of an acid catalyst, where p-toluenesulfonic acid is preferred, in a suitable solvent such as toluene, xylene, cyclohexane, or heptane, where heptane is preferred. The mixture is heated in order to form an acetal and distill out the water formed.

The novel acetals so obtained can be isolated by distillation, or preferably further reacted with a catalytic amount of acid, such as p-toluenesulfonic acid or citric acid, where citric acid is preferred, with or without a solvent. Suitable solvents are heptane, toluene, xylene, or mesitylene. When the theoretical amount of allylic alcohol has been removed the final product is obtained by heating at 165°–200° C., preferably 165°–175° C.

This final rearrangement is known as a Claisen reaction and it can be conveniently monitored by vapor phase chromatography (VPC). T. Massó, A. Portella, and E. Rus, Perfumer And Flavorist, 15, 39 (1990) and references cited therein. The Claisen reaction can take from one to eight hours with three hours usually sufficient.

The so obtained α-allylated aldehydes are novel and some exhibit useful odor properties. However their major function is as intermediates for the final products. These new aldehydes are shown in the following table along with their odor description. The aldehydes are formed as mixtures of diastereomeric isomers.

α-Allylated Aldehydes

| Compound | Odor | Compound | Odor |
|---|---|---|---|
| (structure, CHO) | Fresh pine Camphoraceous | (structure, CHO) | Woody Amber |
| (structure, CHO) | Wormwood Carps N112 | (structure, CHO) | Woody Amber Weak |
| (structure, CHO) | Fruity Fresh Aldehydic green Muget | (structure, CHO) | Fruity |
| (structure, CHO) | Pine Balsam | (structure, CHO) | Fresh Leafy Green |
| (structure, CHO) | Woody Amber | (structure, OHC) | Berry Butyric |

α-Allylated Aldehydes

| Compound | Odor | Compound | Odor |
|---|---|---|---|
| (structure with CHO) | Woody Fruity Camphoraceous | (structure with OHC) | Fruity Sweet Raspberry |
| (structure with CHO) | Floral Quinoline | (structure with OHC) | Weak |
| (structure with CHO) | Woody | (structure with CHO) | Camphoraceous |
| (structure with CHO) | Piney woody | (structure with CHO) | Camphoraceous |
| (structure with CHO) | Fruity | (structure with CHO) | |
| (structure with CHO) | Fruity Weak | | |

The α-allylated aldehydes can be reduced to alcohol derivatives by the usual reducing agents. These include lithium aluminum hydride (LAH), sodium borohydride, or aluminum isopropoxide/isopropanol with the latter being preferred based on the economy of the reagents. The aforementioned reagents deliver a hydride to the aldehyde; however, alkyl groups $C_1$–$C_3$ are readily formed by the addition of methyl, ethyl, or propyl Grignard reagents, or the analogous li-thium reagent. These compounds with $R_4$=H, or $CH_3$, are shown in the following table along with their odor description. They are novel and are used as intermediates for the synthesis of the product THF derivatives. The alcohols are formed as mixtures of diastereomeric isomers.

| Compound | Odor | Compound | Odor |
|---|---|---|---|
| 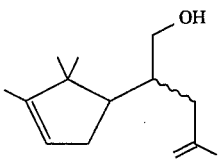 | Weak woody Amber | 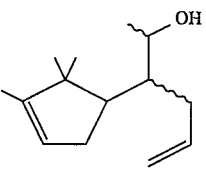 | Barthy woody Musty Cedar |
| 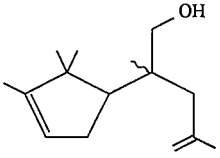 | Weak | 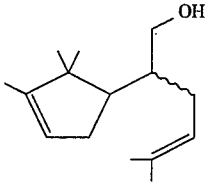 | Weak Floral Rosey Honey |
| 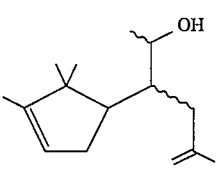 | Amber Woody | 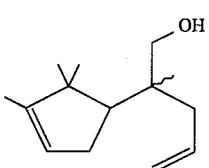 | Weak Floral |
| 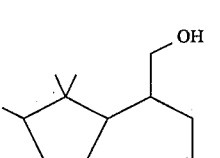 | Weak Woody | 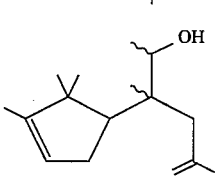 | Weak Woody |
| 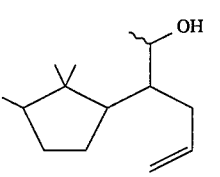 | Woody Pine | 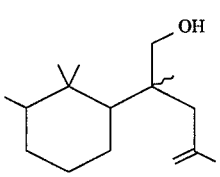 | Weak Fruity |
| 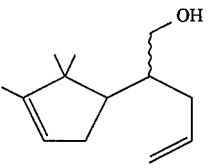 | Fresh Fruity Minty Spicy Woody | 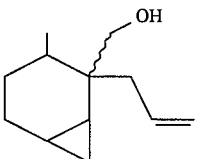 | Camphoraceous |
| 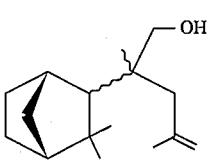 | Weak | 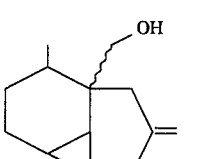 | Woody |
| 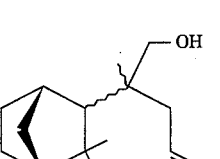 | Weak Woody | 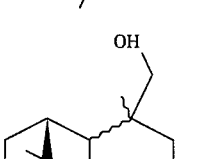 | Weak |

| Compound | Odor | Compound | Odor |
|---|---|---|---|
| [structure] | Weak | [structure] | Weak |
| [structure] | Weak | [structure] | Weak |
| [structure] | Weak | [structure] | Weak |
| [structure] | | [structure] | |
| [structure] | Weak | [structure] | |

The cyclization of these alcohols is accomplished by the catalytic action of p-toluenesulfonic acid, 62% $H_2SO_4$, or amberlyst-15. Other acids also are useable. The solvents appropriate for this cyclization are pentane, hexane, heptane, or toluene, with hexane and heptane being especially preferred. The temperature of the reaction is most easily set at the reflux point of the solvent. The time of the reaction can vary between 1–24 hours, with 1–5 hours being especially preferred.

A special case is the one where 2,2,3-trimethyl-3-cyclopenten-1-yl is attached to the pentenol fragment. The choice of the acid catalyst determines the structure of the product. With p-toluenesulfonic acid in hexane, the product is a 4-(2,2,3-trimethyl-3-cyclopenten-1-yl)tetrahydrofuran derivative (mixture of diastereomers). Whereas, with amberlyst-15 or other strong protic acids, in hexane or heptane, the product is a 4-(2,3,3-trimethyl-1-cyclopenten-1-yl)tetrahydrofuran derivative.

In the second process (Method 2), a primary or secondary aldehyde (R=H, $CH_3$) is treated with an allylic halide under the influence of a strong base in a dipolar aprotic solvent such as dimethylformamide (DMF), or dimethylacetamide (DMA), or tetra methylethylenediamine (TMEDA). DMF is the most preferred solvent and potassium tertbutoxide is a preferred base. Potassium tert-amylate, sodium, or potassium amide are also acceptable.

The resulting mixture of oxygen and carbon alkylates is heated at 165° C. to 185° C. for an appropriate amount of time, until the oxygen alkylate has converted via the Claisen rearrangement to the carbon alkylated product. This product can be a mixture of diastereomers. The details of the process are shown below.

Method 2

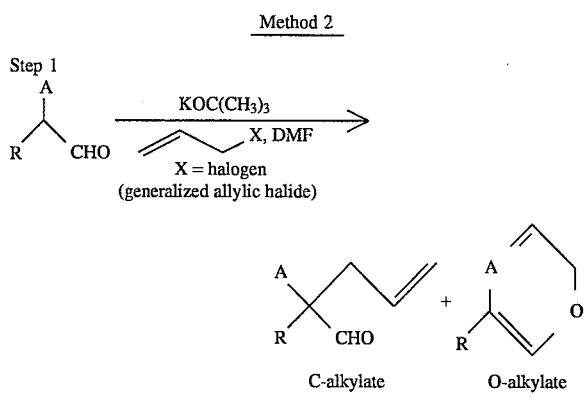

-continued

Method 2

Step 2

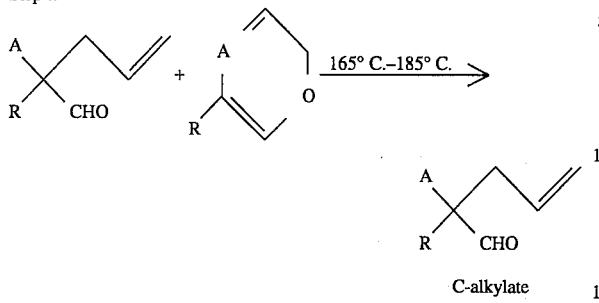

C-alkylate

The so formed a-allylated aldehyde is now treated as in the first process (Method 1); that is, reduction to the alcohol using such reductants as lithium aluminum hydride, sodium borohydride, or aluminum isopropoxide/isopropanol, or any of a number of other aluminum alkoxides. The alcohol can be obtained as a mixture of diastereomers. The so obtained alcohol is then cyclized to a THF, or THP derivative using a suitable acid catalyst. Suitable acid catalysts include p-toluenesulfonic acid, methanesulfonic acid, sulfuric acid, or Amberlyst 15. Suitable solvents for this reaction include pentane, hexane, heptane, toluene or xylene. Hexane and heptane are most preferred. The details of this method are shown below.

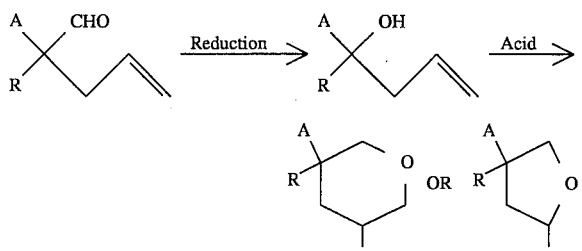

The odor of many of these THF derivatives are characterized as woody-amber. The formation of an amber odor is a very desirable element. There are no examples of amber aroma chemicals with the substitution pattern embodied in this patent application. An amber aroma chemical that is inexpensive to produce would be advantageous. Many of these aforementioned THF derivatives are derived from inexpensive starting materials and consequently the product THF or THP derivatives are themselves inexpensive to produce. THF and THP derivatives in accordance with the invention are shown in the following tables along with their odor description.

The following compounds are preferred: 2,2,4-trimethyl-4-(2,2,3-trimethyl-3-cyclopenten-1-yl)tetrahydrofuran (mixture of diastereomers), 2,2-dimethyl-4-(2,2,3-trimethylcyclopentan-1-yl)tetrahydrofuran (mixture of diastereomers), 2,2-dimethyl-4-(2,3,3-trimethylcyclopentan-1-yl)tetrahydrofuran (mixture of diastereomers), 2,2-dimethyl-4-(3,3-dimethylbicyclo[2.2.1]heptan-2-yl)tetrahydrofuran (mixture of diastereomers), 2,4-dimethyl-4-(3,3-dimethylbicyclo[2.2.1]heptan-2-yl)tetrahydrofuran (mixture of diastereomers), 2,2,4-trimethyl-4-(3,3-dimethylbicyclo[2.2.1]-heptan-2-yl)tetrahydrofuran (mixture of diastereomers), 2,2,5-trimethyl-4-(3,3-dimethylbicyclo[2.2.1]heptan-2-yl)tetrahydrofuran (mixture of diastereomers), 6,8-methano-3,3,7,7,11-pentamethyl-2-oxaspiro[4,5]decane (mixture of diastereomers).

The most preferred compounds are: 2,2,4-trimethyl-4-(2,2,3-trimethyl-3-cyclopenten-1-yl)tetrahydrofuran (mixture of diastereomers), 2,4-dimethyl-4-(3,3-dimethylbicyclo[2.2.1]heptan-2-yl)tetrahydrofuran (mixture of diastereomers), 2,2,4-trimethyl-4-(3,3dimethylbicyclo[2.2.1]heptan-2-yl)tetrahydrofuran (mixture of diastereomers), 6,8-methano3,3,7,7,11-pentamethyl-2-oxaspiro[4.5]decane (mixture of diastereomers).

EXAMPLES $^1$H-NMR spectra were obtained in CDCl$_3$ with (CH$_3$)$_4$Si as an internal standard. $^{13}$C-NMR spectra were obtained in CDCl$_3$ with (CH$_3$)$_4$Si as an internal standard. VPC were run using a J & W 30 m DB-Wax capillary column using helium as the carrier gas.

Example 1

2-(2,2,3-Trimethylcyclopent-3-en-1-yl)-4-methyl-4-pentenal (mixture of diastereomers)

A 2 liter 3 neck flask equipped with a Dean-Stark trap, condenser, thermometer, mechanical agitator, and nitrogen inlet and outlet was charged with 392.5 g of 2,2,3-trimethylcyclopent3-en-1-yl acetaldehyde at a purity of 88.9% (2.30 moles), 415 g of 2-methyl-2-propen-1-ol (5.64 moles), 0.2 g of p-TSA and 1 liter of heptane. The contents were brought to reflux and 43 ml of water were collected. The batch was cooled and washed with 2×250 ml of 10% sodium hydroxide. The batch was dried (MgSO$_4$), filtered and concentrated in vacuo to yield 671 g of crude 2,2,3-trimethylcyclopent-3-en-1-yl acetaldehyde bis-(2-methyl-2-propenyl) acetal. BP 88° C./1.0 mmHg; $^1$H-NMR (300 MHz), δ0.76 (3H, s), 0.98 (3H, s), 1.58 (1H, m), 1.61 (3H, s), 1.76 (6H, s), 1.86–2.0 (3H, m), 2.31 (1H, br s), 3.88–4.04 (4H, m), 4.65 (1H, m), 4.87 (2H, s), 4.89 (2H, s), 5.22 (1H, s); $^{13}$C-NMR (75 MHz), δ12.74, 19.87, 19.91, 25.71, 33.98, 35.88, 46.20, 47.10, 69.00, 69.72, 102.28, 112.27, 112.35, 122.36, 142.84, 148.98; IR (Neat), 1130, 1000 cm$^{-1}$; MS (m/e), 206 (M$^+$-72), 108 (Base); The crude acetal, with 3 g of citric acid added, was distilled through a 10" saddle packed column at a pressure of 115 mmHg. A total of 185.6 g of lights was distilled out between 68°–115° C. The batch was now heated under nitrogen at 160° C. for 3 hours. The batch was now distilled to afford 320.1 g of purified product (74% yield). BP 81° C./0.4 mmHg; $^1$H-NMR (300 MHz), δ0.88 (3H, s), 0.96 (3H, s), 1.59 (3H, s), 1.71 (3H, s), 1.9–2.4 (5H, m), 2.65 (1H, m), 4.71 (1H, s), 4.76 (1H, s), 5.24 (1H, s), 9.49 (1H, d, J=5.43 Hz); $^{13}$C-NMR (75 MHz), δ12.64, 20.26, 22.67, 26.34, 34.19, 37.57, 47.24, 50.47, 52.29, 113.20, 121.39, 143.01, 149.47, 205.82; IR (Neat), 3080, 3050, 2950, 2715, 1730, 1655 cm$^{-1}$; MS (m/e), 206 (M$^+$), 108 (Base);

Odor: Wormwood Corps N-112

Example 2

2-(2,2,3-Trimethylcyclopent-3-en-1-yl)-4-methyl-4-pentenol (mixture of diastereomers)

A 500 ml 3 neck flask was charged with 250 ml of ethanol and 6.0 g of sodium borohydride (0.16 mole). To the flask maintained at 0° C. in an ice bath was added dropwise 74.6 g of the aldehyde from example 1 at a purity of 84.3% (0.30 mole) in 100 ml of ethanol. The batch was stirred 45 minutes at 0° C. The reaction was now quenched by the addition of 50 ml of 25% hydrochloric acid at 0°–5° C. The mixture was poured onto 300 ml of brine and extracted with 3×100 ml of hexane. The hexane was washed with 2×250 ml of brine, dried with magnesium sulfate, filtered, and concentrated in vacuo. The batch was distilled through a 10 cm vigreaux column to afford 48 g of purified product (58% yield). BP 78° C./0.25 mmHg; $^1$H-NMR (300 MHz), δ0.91 (3H, s), 1.09 (3H, s), 1.60 (3H, s), 1.77 (3H, s), 1.85–2.30 (7H, m), 3.66 (2H, m), 4.80 (2H, s), 5.24 (1H, s); $^{13}$C-NMR (75 MHz), δ12.90, 20.20, 22.76, 27.36, 34.07, 39.57, 40.61, 47.53, 50.32, 64.52, 112.63, 122.26, 146.38, 149.32; IR (Neat), 3370, 2960, 2940, 1650, 1040 cm$^{-1}$; MS (m/e), 208 (M$^+$), 95 (Base).

Example 3

2,2-Dimethyl-4-(2,2,3-trimethylcyclopent-3-en-1-yl)-tetrahydrofuran (mixture of diastereomers)

A 500 ml 3 neck round bottomed flask was charged with 56.1 g of 2-(2,2,3-trimethylcyclopent-3-en-1-yl)-4-methyl-4-pentenol, (0.26 mole), 260 ml of hexane, and 0.75 g of p-TSA. The mixture was then refluxed for 7 hours. After cooling the batch was washed with 250 ml of 10% sodium carbonate, and once with 250 ml of brine. The batch was dried with magnesium sulfate, filtered, and concentrated in vacuo. The crude product was distilled through a 10 cm micro Vigreaux column to afford 49.6 g of puffted product (90% yield). BP 51°–52° C./0.2 mmHg; $^1$H-NMR (300 MHz), δ0.85 (3H, s), 0.95 (3H, s), 1.22 (3H, s), 1.27 (3H, s), 1.45 (1H, m), 1.58 (3H, s), 1.73 (1H, m), 1.83–2.0 (2H, m), 2.15 (1H, m), 2.40 (1H, m), 3.46 (1H, m, B part of ABX, $J_{AB}$=6.63 Hz, $J_{BX}$=6.63 Hz), 4.07 (1H, t, A part of ABX, $J_{AB}$=6.63 Hz, $J_{AX}$=6.63 Hz), 5.21 (1H, s), $^{13}$C-NMR (75 MHz), δ12.59, 19.93, 26.57, 28.87, 29.09, 35.42, 42.06, 45.82, 47.09, 54.39, 72.08, 79.67, 121.98, 149.07; IR (Neat), 2980, 1055 cm$^{-1}$; MS (m/e), 208 (M$^+$), 193, 177, 43 (Base);

Odor: Woody amber

Example 4

[rac]-2,2-Dimethyl-4-(2,3,3-trimethylcyclopent-1-en-1-yl)tetrahydrofuran

A 250 ml 3 neck round bottomed flask was charged with 12.1 g of the alcohol from Example 2, at 82.7% purity (0.048 mole), 100 ml of heptane, and 1.5 g of Amberlyst-15. The mixture was refluxed under nitrogen for 24 hours. After cooling, the Amberlyst-15 was filtered and the batch was washed with 100 ml of 10% sodium carbonate, and 100 ml of brine. The batch was dried over magnesium sulfate, filtered, and concentrated in vacuo to afford 12.6 g of crude product. The material was distilled on a 10 cm Vigreaux column to afford 8.7 g of purified product (78% yield). BP 58° C./0.40 mmHg; $^1$H-NMR (300 MHz), δ0.95 (6H, s), 1.25 (3H, s), 1.30 (3H, s), 1.53 (3H, s), 1.6 (3H, m), 1.8 (1H, doubled A part of AB spectrum J=8.1 Hz, 12.2 Hz), 2.2 (2H, br m), 3.30 (1H, quintet, C part of ABC system), 3.56 (1H, t, B part of ABC system, $J_{AB}$=8.0 Hz, $J_{BC}$=8.0 Hz), 3.85 (1H, t, A part of ABC $J_{AB}$=8.0 Hz, $J_{AC}$=8.0 Hz) $^{13}$C-NMR (75 MHz), δ9.60, 26.37, 26.81, 28.47, 28.89, 28.95, 38.97, 39.39, 43.52, 47.16, 70.42, 81.18, 132.13, 141.57; IR (Neat), 2980, 1460, 1050 cm$^{-1}$; MS (m/e), 208 (M$^+$), 163 (Base);

Odor: Citrus nootkatone woody

Example 5

2-(2,2,3-Trimethylcyclopent-3-en-1-yl)propanal (mixture of diastereomers)

A 3 liter 3 neck round bottomed flask was charged with 50 g of sodium hydroxide (1.25 moles) in 250 g of methanol. 200 g of paraformaldehyde, 500 g of hexane and 2.5 g of BHA were added and the flask was cooled to 0° C. With fast agitation 500 g of campholenic aldehyde at a purity of 88.9% (2.92 moles) were added dropwise over 70 minutes keeping the temperature at 0°–5° C. The batch was stirred for 3 hours at 0° C. Then 50 ml of water was added and the layers are separated. The water layer was back extracted with 250 ml of hexane. The hexane extracts were combined and washed with 2×500 ml of 10% sodium hydroxide and 3×500 ml of water. The batch was dried and afforded 1163 g of crude 2-(2,2,3-trimethylcyclopent-3-en-1-yl)propenal in hexane. A second batch was prepared analogously affording 1169 g of crude product.

The batches were hydrogenated separately on a Parr shaker using 10 g of 5% Palladium on carbon and 100 ml of 10% sodium carbonate. In this way were obtained 1064 g of crude product which was distilled from 25 g of boric anhydride and 1.5 g of BHA to afford 805 g of purified product (81% yield). BP 51° C./0.3 mmHg; $^1$H-NMR (300 MHz), δ0.93 (3H, s), 1.11 (3H, s), 1.16 (3H, d, J=6.8 Hz), 1.59 (3H, s), 1.9–2.6 (4H, m), 5.21 (1H, s), 9.64 (1H, d, J=3.3 Hz); $^{13}$C-NMR (75 MHz), δ12.38, 13.92, 19.88, 27.12, 33.47, 47.96, 50.84, 51.81, 121.47, 148.30, 204.83; IR (Neat), 2980, 2705, 1725 cm$^{-1}$; MS (m/e), 166 (M$^+$), 108 (Base).

Example 6

2,4-Dimethyl-2-(2,2,3-trimethylcyclopent-3-en-1-yl-4-pentenal (mixture of diastereomers)

A 4 neck 2 liter round bottomed flask was charged with 600 ml of DMF and 160 g of potassium t-butoxide (1.35 moles). Under nitrogen the flask was cooled to 0° C. and 200 g of 2-(2,2,3-trimethylcyclopent-3-en-1-yl)propanal (from Example 5) at 90% purity (1.08 moles) in 100 ml of DMF were added over 40 minutes at 0°–5° C. The reaction was stirred 30 minutes at 0° C. Then 140 g of methallyl chloride (1.54 moles) in 100 ml of DMF were added dropwise over 40 minutes at 5°–15° C. The batch was stirred 30 minutes at 10°–15° C. With good stirring the reaction mixture was poured onto 1 liter of water and extracted with 3×300 ml of hexane. The hexane extract was washed with 2×500 ml of water and 1 liter of brine. The extract was dried and concentrated in vacuo. The crude mixture of C- and O-alkylates, 261.4 g, was heated in a 500 ml 3 neck flask under nitrogen at 165° C. for 6.5 hours. Fractional distillation afforded 239.5 g of purified product (86.8% yield). BP 84° C./0.15 mmHg; $^1$H-NMR (300 MHz), δ0.89 (3H, s), 1.03 (3H, s), 1.11 (3H, s), 1.55 (3H, s), 1.63 (3H, s), 2.20–2.27 (4H, m), 2.53 (1H, m), 4.67 (1H, s), 4.84 (1H, s), 5.27 (1H, s), 9.79 (1H, s); $^{13}$C-NMR (75 MHz), δ12.34, 15.27, 22.25, 24.31, 28.11, 30.89, 46.11, 48.20, 52.83, 56.17, 115.57, 120.98, 1.41.43, 148.00, 207.01; IR (Neat), 2980, 2700, 1725, 1645, 1450, 1380, 895 cm$^{-1}$; MS (m/e), 220 (M$^+$), 205, 191,121,108 (Base), 93, 55, 41;

Odor: Woody amber

Example 7

2-(2,2,3-Trimethylcyclopent-3-en-1-yl)-2,4-dimethyl-4-pentenol (mixture of diastereomers)

A 4 neck 1 liter round bottomed flask was charged with 400 g of dry isopropanol and 100 g of aluminum isopropoxide (0.48 mole). The contents of the flask were refluxed (80° C.) and 200 g of 2,4-dimethyl-2-(2,2,3-trimethylcyclopent-3-en-1-yl)-4-pentenal at 95.2% (0.865 mole) were added dropwise under nitrogen over 80 minutes. The reaction was refluxed for 2 hours. Then the lights were distilled off to a pot temperature of 110° C. After cooling the batch was extracted with 150 ml of 10% sulfuric acid and 300 ml of hexane. The hexane extract was washed with 150 ml of water, 100 ml of 5% sodium carbonate, and 100 ml of brine. After drying with magnesium sulfate, the batch was filtered, concentrated in vacuo and the crude alcohol, 201.1 g, was distilled from 1 g of soda ash to afford 193.6 g of purified product (88% yield). BP 94° C./0.10 mmHg; $^1$H-NMR (300 MHz), δ1.007 (3H, s), 1.02 (3H, s), 1.42 (3H, s), 1.54 (3H, s), 1.83 (4H, br s), 2.0–2.4 (5H, br m), 3.60 (2H, AB quartet, $J_{AB}$=11.1 Hz), 4.75 (1H, s), 4.88 (1H, s), 5.27 (1H, s); $^{13}$C-NMR (75 MHz), δ12.35, 20.07, 22.31, 25.48, 28.38, 30.96, 42.11, 45.10, 48.27, 54.77, 68.48, 114.81, 121.38, 144.22, 148.28; IR (Neat), 3400 br, 2980, 1040 cm$^{-1}$; MS (m/e), 207 (M$^+$-15), 191, 109 (Base).

Example 8

2,2,4-Trimethyl-4-(2,2,3-trimethylcyclopent-3-en-1-yl)tetrahydrofuran (mixture of diastereomers)

A 1 liter 3 neck round bottomed flask was charged with 600 ml of heptane, 155.3 g of 2-(2,2,3-trimethylcyclopent-3-en-1-yl)-2,4-dimethyl-4-pentenol at 97.7% (0.68 mole) and 0.9 g of p-TSA. The batch was refluxed under nitrogen for 26 hours. Then batch was cooled and washed with 500 ml of 10% sodium carbonate, 500 ml of water and 500 ml of brine. The batch was dried with magnesium sulfate, filtered, and concentrated in vacuo to afford 163.3 g of crude product. Distillation of the product afforded 150.3 g of purified product (92.7%). BP 84° C./0.5 mmHg; $^1$H-NMR (300 MHz), δ0.92 (3H, s), 1.10 (3H, s), 1.20 (3H, s), 1.25 (3H, s), 1.33 (3H, s), 1.55 (4H, sharp m), 1.81–1.99 (2H, m), 2.16 (2H, br m), 3.60 (2H, AB quintet J=8.7 Hz), 5.24 (1H, s); $^{13}$C-NMR (75 MHz), δ12.35, 22.03, 24.57, 25.66, 28.69, 29.96, 32.48, 47.38, 48.36, 50.58, 57.22, 77.63, 80.60, 121.20, 148.01; IR (Neat), 3020, 2980, 1450, 1060 cm$^{-1}$; MS (m/e), 222 (M$^+$), 207, 191, 95, 43;

Odor: Woody amber musky

Example 9

2,2-Dimethyl-4-(2,2,3-trimethylcyclopent-1-yl)-tetrahydrofuran (mixture of diastereomers)

42.3 g of 2,2-Dimethyl-4-(2,2,3-trimethylcyclopent-3-en-1-yl)tetrahydrofuran (from Example 3), at a purity of 98.7% (0.20 mole) were hydrogenated on a Parr shaker using 1.0 g of 5% Pd on carbon. The crude product, 42.5 g, was distilled to afford 41.2 g of purified tetrahydrofuran (98% yield). BP 59° C./0.2 mmHg; $^1$H-NMR (300 MHz), δ0.60 (3H, s), 0.82 (6H, s), 1.20 (3H, s), 1.25 (3H, s), 1.2–1.4 (2H, m), 1.6–2.0 (6H, m), 2.25 (1H, m), 3.42 (1H, B part of ABX, $J_{AB}$=7.73 Hz, $J_{BX}$=7.73 Hz), 4.06 (1H, A part of ABX, $J_{AB}$=7.73 Hz, $J_{AX}$=7.73 Hz); $^{13}$C-NMR (75 MHz), δ13.74, 14.84, 26.55, 26.94, 28.10, 29.08, 29.14, 30.18, 42.68, 45.53, 45.96, 54.92, 71.90, 79.48; IR (Neat), 2980, 1470, 1050 cm$^{-1}$; MS (m/e), 195 (M$^+$-15 Base);

Odor: Amber woody

Example 10

2,2-Dimethyl-4-(2,3,3-trimethylcyclopent-1-yl)-tetrahydrofuran (mixture of diastereomers)

31.7 g of [rac]-2,2-dimethyl-4-(2,3,3-trimethylcyclopent-1-en-1-yl)tetrahydrofuran (from Example 4), at a purity of 92.7% (0.14 mole) were hydrogenated on a Parr shaker using 2.0 g of 5% Pd on carbon in 50 ml of ethanol. The product, 31.6 g, was distilled to afford 30 g (100% yield). BP 52°–54° C./0.2 mmHg; $^1$H-NMR (300 MHz), δ0.74 (3H, s), 0.85 (3H, d, J=6.9 Hz), 0.94 (3H, s), 1.2 (1H, m), 1.19 (3H, s), 1.28 (3H, s), 1.3–1.6 (5H, m), 1.65–1.95 (2H, m), 2.33 (1H, m), 3.47 (1H, m), 3.94 (1H, m); $^{13}$C-NMR (75 MHz), δ13.83, 22.07, 26.75, 28.29, 28.56, 28.82, 40.64, 43.57, 44.72, 45.76, 49.56, 49.69, 71.84, 81.25; IR (Neat), 2980, 1460, 1055 cm$^{-1}$; MS (m/e), 195 (M$^+$-15), 137, 43 (Base);

Odor: Amber woody labdanum

Example 11

3-(2,2,3-Trimethylcyclopent-3-en-1-yl)-5-methyl-5-hexen-2-ol (mixture of diastereomers)

A 500 ml 3 neck round bottomed flask was charged with 27.3 g of 4-methyl-2-(2,2,3-trimethylcyclopent-3-en-1-yl)-4-pentenal (from Example 1) (0.127 mole) in 150 ml of dry ether. The flask was cooled to 0° C. and 55 ml of 3.0M methylmagnesium bromide (0.165 mole) was added over 30 minutes and stirred 30 minutes at 5° C. The reaction was quenched by the addition of 100 ml of saturated ammonium chloride. The layers were separated and the aqueous was extracted with 2×50 ml of ether. The organic extracts were combined, washed with 200 ml of brine, dried, filtered, and concentrated in vacuo to afford 28.6 g of crude alcohol. Distillation afforded 18.1 g of product (64% yield). BP 88° C./0.3 mmHg; $^1$H-NMR (300 MHz), δ0.87 (3H, s), 1.00 (3H, s), 1.21 (3H, d, J=8.91 Hz), 1.60 (3H, br s), 1.60 (1H, m), 1.79 (3H, s), 1.82–2.27 (6H, m), 4.00 (1H, m), 4.70 (2H, m), 5.27 (1H, s); $^{13}$C-NMR (75 MHz), δ 12.70, 20.11, 22.42, 26.24, 33.19, 36.88, 37.78, 40.66, 47.51, 49.43, 70.11, 112.53, 122.60, 146.92, 148.23; IR (Neat), 3400, 2980, 1650, 1140, 1080 cm$^{-1}$; MS (m/e), 222 (M$^+$), 43 (Base);

Odor: Woody amber weak

Example 12

2,2,5-Trimethyl-4-(2,3,3-trimethylcyclopent-1-en-1-yl)tetrahydrofuran (mixture of diastereomers)

A 125 ml 3 neck flask was charged with 7.0 g of the alcohol in Example 11 (0.03 mole), 75 ml of heptane and 0.7 g of Amberlyst-15. The mixture was refluxed for 24 hours. After cooling and filtration of the Amberlyst-15, the batch was washed with 100 ml of 10% sodium carbonate, and 100 ml of brine. The batch was dried, filtered, and concentrated in vacuo to afford 7.5 g of product. The crude product was distilled to afford 5.2 g of purified product (74.3% yield). BP 54° C./0.1 mmHg; $^1$H-NMR (300 MHz), δ0.97 (6H, s), 1.12 (3H, d, J=5.14 Hz), 1.28 (3H, s), 1.29 (3H, s), 1.54 (3H, s), 1.57 (2H, m), 1.77 (2H, d, J=9.57 Hz), 2.18 (2H, br m), 2.7 (1H, m), 3.81 (1H, m); $^{13}$C-NMR (75 MHz), δ9.67, 19.71, 26.15, 26.54, 29.87, 30.01, 30.15, 39.90, 44.17, 46.96, 47.16, 77.36, 79.72, 131.32, 142.52; IR (Neat), 2980, 1460, 1095 cm$^{-1}$; MS (m/e), 222 (M$^+$), 163 (Base);

Odor: Woody spicy balsamic

Example 13

2,2,5-Trimethyl-4-(2,2,3-trimethylcyclopent-3-en-1-yl)tetrahydrofuran (mixture of diastereomers)

A 500 ml 3 neck flask was charged with 58.8 g of the alcohol from Example 11 at 91.2% (0.24 mole), 250 ml of hexane, and 0.7 g of p-TSA. The mixture was refluxed for 12 hours. After cooling the mixture was washed with 250 ml of 10% sodium carbonate, and 250 ml of brine. The mixture was dried with sodium sulfate, filtered, and concentrated in vacuo to afford 57.1 g of crude product which was distilled to afford 47.9 g of product (90% yield). BP 61° C./0.05 mmHg; $^1$H-NMR (300 MHz), a complex mixture of at least 3 diastereomers. Spectra consistent with assigned structures; $^{13}$C-NMR (75 MHz), spectra consistent with complex mixture of at least 3 diastereomers; IR (Neat), 2980, 1460, 1100, 1080 cm$^{-1}$; MS (m/e), 222 (M$^+$);

Odor: Amber woody animal

Example 14

2,2,5-Trimethyl-4-(2,2,3-trimethylcyclopent-1-yl)tetrahydrofuran (mixture of diastereomers)

The tetrahydrofuran mixture from Example 13, 35.5 g at 96.7% (0.154 mole) was hydrogenated at 60 psi at 40°–50° C. using 0.75 g of 5% Pd on carbon. The crude product, 35.7 g, was distilled to yield 34.4 g of purified product (100% yield). BP 53° C./0.04 mmHg; $^1$H-NMR (300 MHz), spectra consistent with assigned structures. $^{13}$C-NMR (75 MHz), spectra consistent with assigned structures. IR (Neat), 2990, 1490, 1130, 1110 cm$^{-1}$; MS (m/e), 209 (M$^+$-15), 110, 96 (Base);

Odor: Woody camphoraceous

Example 15

2,2,5-Trimethyl-4-(2,3,3-trimethylcyclopent-1-yl)tetrahydrofuran (mixture of diastereomers)

The mixture of tetrahydrofurans from Example 12, 19.8 g (0.09 mole) was hydrogenated with 0.5 g of 5% Pd on carbon in acetic acid at 100°–110° C. The resulting crude product, 16.9 g, was distilled affording 14.8 g of a mixture of tetrahydrofurans (74% yield). BP 72° C./0.30 mmHg; $^1$H-NMR (300 MHz), spectra consistent with assigned structures; $^{13}$C-NMR (75 MHz), spectra consistent with assigned structures; IR (Neat), 2980, 1460, 1080 cm$^{-1}$; MS (m/e), 209 (M$^+$-15), 191, 110, 96, 43 (Base);

Odor: Woody amber camphoraceous

Example 16

3,5-Dimethyl-3-(2,2,3-trimethylcyclopent-3-en-1-yl)-5-hexen-2-ol (mixture of diastereomers)

Similar to Example 11, 11.7 g of 2,4-dimethyl-2-(2,2,3-trimethylcyclopent-3-en-1-yl)-4-pentenal (from Example 6), at 94% (0.05 mole) was treated with 30 ml of 3.0M methylmagnesium bromide (0.09 mole). This afforded 12.2 g of crude alcohol (>95% yield). BP 110° C./0.1 mmHg (Kugelrohr); $^1$H-NMR (300 MHz), δ1.02 (3H, s), 1.12–1.2 (9H, multiple s), 1.55 (3H, s), 1.87 (3H, multiple s), 2.2–2.6 (6H, m), 3.7–4.0 (1H, m) 4.86 (2H, m), 5.2 (1H, multiple s); $^{13}$C-NMR (75 MHz), δ12.35, 18.03, 19.58, 22.76, 25.32, 28.79, 31.09, 41.62, 44.56, 48.88, 54.46, 74.54, 115.06, 122.05, 145.27, 148.19; IR (Neat), 3500, 2980, 1640, 1450, 1080, 900 cm$^{-1}$; MS (m/e), 236 (M$^+$), 221, 108 (Base).

Example 17

2,2,4,5-Tetramethyl-4-(2,2,3-trimethylcyclopent-3-en-1-yl)tetrahydrofuran (mixture of diastereomers)

Similar to Example 13, 10.7 g of the alcohol from Example 16 at 95.7% (0.045 mole), 70 ml of hexane, and 0.2 g of p-TSA were refluxed under nitrogen for 7 hours. The usual work-up afforded 10.6 g of crude product. The crude product was distilled to afford 8.9 g of purified product (87% yield). BP 62° C./0.1 mmHg; $^1$H-NMR (300 MHz), spectra consistent with assigned structures; $^{13}$C-NMR (75 MHz), spectra consistent with assigned structures; IR (Neat), 2980, 1455, 1120, 1110 cm$^{-1}$; MS (m/e), 236 (M$^+$), 221, 191, 177, 108 (Base);

Odor: Amber woody leather animalic

Example 18

2-(2,2,3-trimethylcyclopent-1-yl)acetaldehyde 510 g of 2-(2,2,3-trimethylcyclopent-3-en-1-yl) acetaldehyde at 85% (2.85 moles) were hydrogenated with 20 g of 5% Pd on carbon (50% wet) with 10 g of soda ash at 60 psi and 50°–60° C. The crude product was distilled from 22 g of boric anhydride affording 324 g of purified product, containing pinocamphone as a 10–15% impurity. BP 48° C./0.6 mmHg; $^1$H-NMR (300 MHz), δ0.54 (3H, s), 0.87 (3H, d, J=6.6 Hz), 0.88 (3H, s), 1.1–1.4 (2H, m), 2.25 (1H, m), 2.50 (1H, m), 2.55 (1H, m), 2.70–2.95 (3H, br m), 9.76 (1H, br s); $^{13}$C-NMR (75 MHz), δ14.01, 14.73, 25.54, 28.34, 30.35, 42.62, 44.84, 45.03, 45.75, 203.83; IR (Neat), 2980, 2720, 1730, 1470, 1390, 1370 cm$^{-1}$; MS (m/e), 139 (M$^+$-15), 97, 69 (Base).

Example 19

2,2,3-Trimethylcyclopent-1-yl acetaldehyde-bis-(2-propenyl acetal)

In a similar procedure as in Example 1, 75.5 g of 2,2,3-trimethylcyclopent-1-yl acetaldehyde (from Example 18) at 84.4% (0.41 mole), 52 g of allyl alcohol (0.9 mole), 250 ml of heptane and 0.25 g of p-TSA were combined and refluxed until water ceases distilling. The product was cooled, washed with 100 ml of 10% sodium carbonate, dried, filtered, and concentrated. The crude product was distilled from 2 g of soda ash affording 69 g of product acetal (66% yield). BP 74° C./0.05 mmHg; $^1$H-NMR (300 MHz), δ0.51 (3H, s), 0.82 (3H, d, J=6.84 Hz), 0.87 (3H, s), 1.2–1.6 (5H, m), 1.81 (3H, m), 4.0 (4H, m), 4.6 (1H, dd, J=3.9, 7.95 Hz), 5.16 (2H$_A$, d, J$_{AX}$=10.3 Hz), 5.30 (2H$_B$, dd, J$_{BX}$=16.9 Hz, J$_{AB}$=1.71), 5.9 (2H, m); $^{13}$C-NMR (75 MHz), δ13.98, 14.48, 25.59, 28.38, 30.44, 34.42, 42.56, 44.99, 46.48, 65.53, 66.83, 102.21, 116.93, 117.01, 135.38, 135.42; IR (Neat), 2960, 1650, 1470, 1125, 1040, 1000, 920 cm$^{-1}$; MS (m/e), 195 (M$^+$-57);

Odor: Weak fatty

Example 20

2-(2,2,3-Trimethylcyclopent-1-yl)-4-pentenal (mixture of diastereomers)

A 125 ml 3 neck flask was charged with 60.1 g of the acetal at 82.9% (0.198 mole) from Example 19, and 1.0 g of citric acid. The flask was heated under nitrogen to a pot temperature of 200° C. when 14.5 ml (12.2 g) of allyl alcohol distills off. The batch was now heated at 150° C. for 2 hours. The crude aldehyde, 47.6 g, was distilled to afford 35.2 g of purified product (92%). BP 75° C./0.2 mmHg; $^1$H-NMR (300 MHz), δ0.62 (3H, s), 0.82 (3H, d, J=6.72 Hz), 0.84 (3H, s), 1.2–1.9 (6H, m), 2.3 (2H, br s), 2.43 (1H, br s), 5.04 (2H, m), 5.7 (1H, m), 9.5 (1H, s); $^{13}$C-NMR (75 MHz), δ13.69, 14.90, 26.47, 29.43, 33.42, 42.69, 45.63, 50.49, 52.93, 54.64, 117.51, 135.40, 206.36; IR (Neat), 2980, 2705, 1730, 1420 cm$^{-1}$; MS (m/e), 194 (M$^+$), 179, 152, 137, 109, 69 (Base);

Odor: Pine balsamic

Example 21

2-(2,2,3-Trimethylcyclopent-1-yl)-4-pentenol (mixture of diastereomers)

Similar to Example 2, 30.0 g of the aldehyde from Example 20, at 94.6% (0.146 mole), 2.7 g of sodium borohydride (0.071 mole) and 100 ml of ethanol give in the usual manner 29.2 g of crude alcohol which afforded after distillation 23.5 g of purified product (82% yield). BP 72° C./0.18 mmHg; $^1$H-NMR (300 MHz), δ0.62 (3H, s), 0.82 (3H, d, J=6.78 Hz), 0.96 (3H, s), 1.1–1.9 (8H, m), 2.0–2.3 (2H, m), 3.5–3.75 (2H, m), 5.05 (2H, m), 5.91 (1H, m); $^{13}$C-NMR (75 MHz), δ13.83, 14.77, 26.15, 26.93, 29.82, 34.32, 41.83, 42.70, 45.80, 50.29, 64.23, 116.42, 138.10; IR (Neat), 3350, 2980, 1640, 1470, 1370, 1045, 910 cm$^{-1}$; MS (m/e), 178 (M$^+$-16), 163, 109, 69 (Base);

Odor: Weak woody

Example 22

2-Methyl-4-(2,2,3-trimethylcyclopent-1-yl)tetrahydrofuran (mixture of diastereomers)

Similar to Examples 4, 15.4 g of the alcohol from Example 21 at 95.9% (0.075 mole), 75 ml of heptane, and 1.0 g of Amberlyst-15, were charged to a flask and refluxed for 4 hours. After the usual work-up the crude product, 17.0 g, was distilled affording 11.5 g of pure product (78%); BP 48° C./0.04 mmHg; $^1$H-NMR (300 MHz), δ0.60 (3H, s), 0.80 (3H, d, J=6.84 Hz), 0.83 (3H, s), 1.21 (3H, d, J=5.97 Hz), 1.1–1.85 (7H, m), 2.2 (2H, m), 3.2–3.5 (1H, m), 4.0 (2H, m); $^{13}$C-NMR (75 MHz), δ13.78, 14.85, 21.32, 26.86, 28.08, 30.18, 39.17, 41.44, 43.33, 46.53, 55.08, 72.02, 74.74; IR (Neat), 2980, 1470, 1370, 1100, 1050, 1020 cm$^{-1}$; MS (m/e), 196 (M$^+$), 181, 41 (Base).

Odor: Woody fruity

Example 23

3-(2,2,3-Trimethylcyclopent-1-yl)-5-hexen-2-ol (mixture of diastereomers)

Similar to Example 11, 76.5 g of the aldehyde from Example 20 at 90% purity (0.355 mole) in 250 ml of dry ether was treated with 130 ml of 3.0M methylmagnesium bromide (0.39 mole). This afforded after work-up 80.5 g of crude alcohol. Distillation from 2 g of soda ash afforded 69 g of purified alcohol (93% yield). BP 84° C./0.1 mmHg; $^1$H-NMR (300 MHz), spectra consistent with assigned structures, $^{13}$C-NMR (75 MHz), δ13.94, 15.32, 20.55, 24.72, 26.30, 29.60, 32.14, 33.52, 43.11, 44.75, 48.67, 69.31, 115.41, 139.25; IR (Neat), 3380, 2980, 1640, 1470, 1370, 910 cm$^{-1}$; MS (m/e), 195 (M$^+$-15), 177, 123, 109, 69 (Base);

Odor: Woody pine

Example 24

2,5-Dimethyl-3-(2,2,3-trimethylcyclopent-1-yl)tetrahydrofuran (mixture of diastereomers)

Similar to Example 4, 37.4 g of the alcohol from Example 23 at 90% purity (0.16 mole) was treated with 2.0 g of Amberlyst-15, in 250 ml of heptane. After 2 hours at reflux, the reaction was complete. The usual work-up afforded 40 g of crude product which was distilled to afford 30.3 g of purified tetrahydrofuran (91% yield). BP 50° C./0.1 mmHg; $^1$H-NMR (300 MHz) spectra consistent with assigned structures; $^{13}$C-NMR (75 MHz) spectra consistent with assigned structures; IR (Neat), 2980, 1460, 1380, 1100, 1070 cm$^{-1}$; MS (m/e), 210 (M$^+$), 195, 166, 151, 124, 109, 82 (Base);

Odor: Woody fresh

Example 25

3-(2,2,3-Trimethylcyclopent-3-en-1-yl)-5-methyl-5-hexen-2-one (mixture of diastereomers)

The alcohol from Example 11, 74.6 g at 90.8% purity (0.31 mole) was added at 0° C. to a mixture of 150 g of pyridinium chlorochromate (0.522 mole) in 1000 ml of methylene chloride. The mixture was stirred for 3 hours at room temperature. Ether, 600 ml, was added and the reaction mixture was stirred for 15 minutes. The organics were decanted from the residue and were filtered through a pad of florisil. The solvents were removed in vacuo and the residue, 67.0 g, was distilled to afford 55 g of product (82% yield). BP 85° C./0.3 mmHg; $^1$H-NMR (300 MHz), δ0.87 (3H, s), 0.92 (3H, s), 1.58 (3H, s), 1.73 (3H, s), 2.11 (3H, s), 2.0–2.3 (5H, m), 2.85 (1H, m), 4.68 (1H, s), 4.75 (1H, s), 5.24 (1H, s), $^{13}$C-NMR (75 MHz), δ13.10, 19.97, 22.60, 26.40, 28.18, 34.51, 40.50, 47.56, 52.31, 53.76, 113.07, 121.36, 143.43, 149.39, 212.95; IR (Neat), 2960, 2940, 1710, 1650, 1465, 1365, 900 cm$^{-1}$; MS (m/e), 220 (M$^+$), 20.5, 177, 108 (Base);

Odor: Woody nootkatone weak citrus

Example 26

2,5-Dimethyl-3-(2,2,3-trimethylcyclopent-3-en-1-yl)-5-hexen-2-ol (mixture of diastereomers)

Similar to Example 11, a 500 ml 3 neck flask was charged with 46.5 g of the ketone from Example 25 at 87.4% purity (0,184 mole) in 250 ml of dry ether. 75 ml of 3.0M methylmagnesium bromide (0.225 mole) were added dropwise. After refluxing for 2 hours, work-up of the reaction in the usual manner afforded 46.6 g of crude alcohol (57.4% alcohol, 27% ketone). Distillation afforded 17.0 g of purified alcohol (39% yield). BP 75° C./0.15 mmHg; $^1$H-NMR (300 MHz), δ0.87 (3H, s), 1.03 (3H, s), 1.19 (3H, s), 1.24 (3H, s), 1.61 (3H, s), 1.87 (3H, s), 1.9–2.4 (7H, m), 4.81 (1H, s), 4.89 (1H, s), 5.27 (1H, s); $^{13}$C-NMR (75 MHz), δ13.19, 21.19, 23.14, 26.39, 26.45, 29.91, 31.83, 38.04, 44.05, 48.84, 50.72, 76.52, 111.65, 122.63, 147.71, 149.63; IR (Neat), 3470, 2970, 1650, 1470, 1380, 1120, 890 cm$^{-1}$; MS (m/e), 236 (M$^+$), 221, 178, 163, 59 (Base).

Example 27

2,2,5,5-Tetramethyl-3-(2,2,3-trimethylcyclopent-3-en-1-yl)tetrahydrofuran

The alcohol from Example 26, 16.6 g at 87.2% purity (0.061 mole), 0.1 g of p-TSA and 100 ml of hexane were heated at 55° C. for approximately 2 hours. The reaction was cooled and worked up as usual to afford 16.7 g of crude product. The product was distilled to afford 12.2 g (85% yield) of purified tetrahydrofuran. BP 72° C./0.3 mmHg; $^1$H-NMR (300 MHz), $\delta$0.79 (3H, s), 1.00 (3H, s), 1.02 (3H, s), 1.21 (3H, s), 1.24 (3H, s), 1.30 (3H, s), 1.62 (3H, s), 1.70–1.95 (3H, m), 2.09 (3H, m), 5.28 (1H, s); $^{13}$C-NMR (75 MHz), $\delta$12.73, 20.10, 24.68, 24.99, 28.95, 30.20, 30.84, 32.16, 42.08, 46.82, 47.90, 48.89, 77.96, 83.21, 122.05, 147.68; IR (Neat), 2980, 1470, 1370, 1135, 990 cm$^{-1}$; MS (m/e), 221 (M$^+$-15), 178, 163, 134, 121,108 (Base,);

Odor: Amber woody

Example 28

2-(2,2,3-Trimethylcyclopent-1-yl)propanal (mixture of diastereomers)

The aldehyde from Example 5, 190 g at 86% purity (0.98 mole) was hydrogenated on a Parr shaker at 60 psi and 70° C. using a total of 8.5 g of 5% Pd on carbon. The crude product, 180 g, was distilled to afford 144 g of purified product (87% yield). BP 53° C./0.6 mmHg; $^1$H-NMR (300 MHz), $\delta$0.64 (3H, s), 0.85 (3H, d, J=6.3 Hz), 1.02 (3H, s), 1.15 (3H, d, J=6.8 Hz), 1.2–1.8 (6H, m), 2.4 (1H, m), 9.61 (1H, s); $^{13}$C-NMR (75 MHz), $\delta$13.72, 14.82, 25.89, 26.48, 27.22, 29.34, 29.99, 45.42, 48.79, 51.80, 205.22; IR (Neat), 2980, 2700, 1730, 1470 cm$^{-1}$; MS (m/e), 168 (M$^+$), 153, 111, 69 (Base);

Odor: Camphor borneol

Example 29

2,4-Dimethyl-2-(2,2,3-trimethylcyclopent-1-yl)-4-pentenal (mixture of diastereomers)

A 1 liter 3 neck flask equipped with a Dean-Stark trap, mechanical agitator, condenser, thermometer and nitrogen sweep was charged with the aldehyde from Example 28, 122.9 g at approximately 90% purity (0.66 mole), 230 g of methallyl alcohol (3.20 moles), 1.0 g of p-TSA, and 500 ml of cyclohexane. The contents were refluxed for 72 hours taking off a water-methallyl alcohol distillate (18 ml). The batch was cooled, washed with 250 ml of 10% sodium carbonate and 250 ml of brine. The mixture was dried, filtered, and concentrated in vacuo to afford 311 g of a mixture of acetal, and starting material. Distillation from 2 g of soda ash afforded 119 g of starting aldehyde. The pot residue 134.8 g contains the crude acetal (IR (Neat), 2980, 1660, 1470, 1150, 1100 cm$^{-1}$) which was taken up in 200 ml of tetraglyme and 3 g of citric acid. Under nitrogen the flask was heated to 185° C. and 4 ml of methallyl alcohol were collected (approximately 2.5 hours). The flask was cooled and the contents were poured into 500 ml of 10% sodium carbonate and extracted with 2×200 ml of ether. The ether was washed with 200 ml of 10% sodium carbonate, 250 ml of water, and 250 ml of brine. The batch was dried, filtered, and concentrated to afford 124.7 g of crude product. Distillation afforded 58 g of purified product (40% yield). BP 92° C./0.3 mmHg; $^1$H-NMR (300 MHz), $\delta$0.64 (3H, s), 0.78 (3H, d, J=6.78 Hz), 0.91 (3H, s), 1.05 (3H, s), 1.60 (3H, s), 1.5–1.9 (6H, m), 2.3 (2H, AB quartet, J$_{AB}$=13.8 Hz), 4.63 (1H, s), 4.81 (1H, s), 9.73 (1H, s); $^{13}$C-NMR (75 MHz), $\delta$13.50, 14.67, 16.73, 23.34, 24.23, 27.84, 28.88, 44.24, 45.95, 46.32, 53.13, 56.56, 115.46, 141.53, 207.14; IR (Neat), 2980, 2700, 1720, 1460, 900 cm$^{-1}$; MS (m/e), 222 (M$^+$), 207, 166, 123, 109, 95, 41 (Base);

Odor: Woody fruity camphoraceous

Example 30

2,4-Dimethyl-2-(2,2,3-trimethylcyclopent-1-yl)-4-pentenol (mixture of diastereomers)

Similar to Example 2, 32.0 g of the aldehyde from Example 29 at 64% purity (0.09 mole), 4.0 g of sodium borohydride (0.10 mole) and 100 ml of ethanol were reacted in the usual way. The crude product, 31.5 g, was distilled to afford 16.2 g of purified alcohol (79% yield). BP 105° C./0.4 mmHg; $^1$H-NMR (300 MHz), $\delta$0.73 (3H, s), 0.76 (3H, s), 0.99 (3H, d, J=5.8 Hz), 1.04 (3H, s), 1.15–1.7 (7H, m), 1.82 (3H, s), 2.1–2.35 (2H, m), 3.6 (2H$_{AB}$, AB quartet, J=12 Hz), 4.74 (1H, s), 4.88 (1H, s); $^{13}$C-NMR (75 MHz), $\delta$13.50, 16.89, 19.82, 23.20, 25.49, 28.49, 29.35, 43.43, 45.01, 45.05, 46.33, 54.46, 68.58, 114.68, 144.26; IR (Neat), 3400, 2980, 1640, 1470, 1370, 1050, 890 cm$^{-1}$; MS (m/e), 209 (M$^+$-15), 193, 168, 151, 43 (Base).

Example 31

2,2,4-Trimethyl-4-(2,2,3-trimethylcyclopent-1-yl)-tetrahydrofuran (mixture of diastereomers)

In a manner similar to Example 4, 15.5 g of the alcohol from Example 30 at 87.5% (0.06 mole), 1.0 g of Amberlyst-15, and 75 ml of hexane were refluxed for 1 hour. The usual work-up afforded 15.5 g of crude product. The crude tetrahydrofuran was distilled to afford 12.3 g of purified product (91% yield). BP 85° C./0.5 mmHg; $^1$H-NMR (300 MHz), $\delta$0.65 (3H, s), 0.78 (3H, d, J=6.78 Hz), 0.98 (3H, s), 1.18 (3H, s), 1.21 (3H, s), 1.32 (3H, s), 1.5–2.0 (8H, m), 3.55 (2H$_{AB}$, AB quartet, J$_{AB}$=8.34 Hz); $^{13}$C-NMR (75 MHz), $\delta$13.46, 16.49, 24.56, 25.51, 28.31, 28.64, 29.78, 29.90, 43.66, 45.92, 47.68, 50.90, 57.46, 77.79, 80.43; IR (Neat), 2980, 1460, 1370, 1060 cm$^{-1}$; MS (m/e), 209 (M$^+$-15), 191, 168, 151, 95, 43 (Base);

Odor: Woody camphoraceous weak

Example 32

[rac]-2,2,4-Trimethyl-4-(2,3,3-trimethylcyclopent-1-en-1-yl)tetrahydrofuran

The tetrahydrofuran from Example 8, 14.3 g at 88.7% purity (0.057 mole), 65 ml of heptane, and 3.5 g of Amberlyst-15 were refluxed under nitrogen for 48 hours. After cooling the Amberlyst-15 was filtered and the organic layer was washed with 100 ml of 10% sodium carbonate and 100 ml of brine. The batch was dried, filtered and concentrated in vacuo to afford 11.1 g of crude product. The product was distilled to afford 7.4 g of purified product (59% yield). BP 59° C./0.3 mmHg; $^1$H-NMR (300 MHz), $\delta$0.94 (3H, s), 0.95 (3H, s), 1.20 (6H, s), 1.32 (3H, s), 1.52 (3H, s), 1.57 (2H, m), 1.9 (2H$_{AB}$, AB quartet, J=12.4 hz), 2.2 (2H, m), 3.7 (2H$_{AB}$, AB quartet, J=8.5 Hz); $^{13}$C-NMR (75 MHz), $\delta$10.93, 25.73, 26.22, 2.6.33, 28.80, 30.02, 31.10, 38.81, 45.96, 47.26, 51.80, 76.50, 80.07, 138.19, 138.41; IR (Neat), 2980, 1460, 1370, 1060 cm$^{-1}$; MS (m/e), 222 (M$^+$), 207, 191, 177, 149, 135, 121 (Base), 108, 107, 43;

Odor: Woody cedar plastic vanillin notes

Example 33

2,2,4-Trimethyl-4-(1,2,2-trimethylbicyclo[3.1.0]hex-3-yl)tetrahydrofuran (mixture of diastereomers)

This example was an application of the procedure given by E. C. Friedrich, S. E. Lumetta, and E. J. Lewis, *J. Org. Chem.*, 54, 2388 (1989).

A 500 ml 4 neck round bottomed flask fitted with a spiral condenser, mechanical agitator, nitrogen inlet, thermometer, rubber septum, and 125 ml pressure equalizing dropping funnel was charged with 44.1 g of zinc dust (0.67 g atom), 6.68 g of copper (I) chloride (0.067 mole), 120 ml of dry ether, 91.5 g (36.9 ml) of dibromomethane (0.526 mole), and 40.8 g of the tetrahydrofuran from Example 8 at a purity of 96% (0.176 mole). Anhydrous titanium (IV) chloride, 2.0 g, (1.12 ml) was added dropwise via syringe through the rubber septum. After the addition the flask was heated at 45° C. for 24 hours, replacing any ether that evaporates using the dropping funnel. The reaction was cooled and carefully poured with stirring into 100 ml of sat. ammonium chloride. Any solids were filtered and the supernatant was washed with 3×100 ml of 10% sodium hydroxide and 100 ml of brine. The organics were dried with magnesium sulfate, filtered, and concentrated in vacuo. The crude product, 38.3 g, was a mixture of 53.4% product and 43.3% starting material. The mixture was separated on a spinning band column to afford 17.0 g of purified product (41% yield). The product was a mixture of two diastereomers 75.4:24.6. BP 60° C./0.08 mmHg; $^1$H-NMR (300 MHz), δ0.01 (1H, dd, J=7.68, 4.65 Hz), 0.43 (1H, dd, J=8.19, 3.99 Hz), 0.88 (3H, s), 0.99 (3H, s), 1.02 (3H, s), 1.04 (1H, m), 1.17 (3H, s), 1.18 (3H, s), 1.24 (1H, m), 1.31 (3H, s), 1.47–1.82 (4H, m), 3.40 (2H$_{AB}$, AB quartet, J$_{AB}$=8.64 Hz); $^{13}$C-NMR (75 MHz), δ 14.44, 17.31, 21.80, 21.99, 25.60, 26.27, 28.42, 28.93, 29.95, 32.04, 42.53, 46.68, 51.03, 52.28, 77.55, 80.72; IR (Neat), 2980, 1460, 1370, 1060 cm$^{-1}$; MS (m/e), 236 (M$^+$), 221, 205, 123, 107, 95, 43 (Base);

Odor: Amber fruity woody

Example 34

2,2,4-Trimethyl-4-(2,2,3,3-tetramethylcyclopent-1-yl)tetrahydrofuran (mixture of diastereomers)

The tetrahydrofuran from Example 33, 12.8 g at 96.7% purity (0.052 mole), 0.5 g of platinum oxide and 50 ml of acetic acid was hydrogenated on a Parr shaker at 55° C. The resulting crude product, 13.5 g, was distilled to afford 11.7 g of purified product (95% yield). BP 69° C./0.08 mmHg; $^1$H-NMR (300 MHz), δ0.76 (3H, s), 0.81 (3H, s), 0.85 (3H, s), 0.91 (3H, s), 1.20 (6H, s), 1.33 (3H, s), 1.38 (1H, m), 1.46–1.81 (5H, m), 1.94 (1H, m), 3.50 (2H$_{AB}$, AB quartet, J$_{AB}$=8.52 Hz); $^{13}$C-NMR (75 MHz), δ20.91, 23.04, 23.92, 24.74, 24.98, 26.49, 28.45, 30.11, 37.47, 44.89, 45.59, 47.86, 49.73, 53.44, 77.94, 80.78; IR (Neat), 2980, 1470, 1370, 1060 cm$^{-1}$; MS (m/e), 238 (M$^+$), 223, 205, 195, 182, 165, 137, 123, 109, 95, 69, 43 (Base);

Odor: Woody fruity

Example 35

2-(2,2,3-Trimethylcyclopent-3-en-1-yl)-5-methyl-4-hexenal (mixture of diastereomers)

A 3 liter 3 neck flask fitted with a mechanical agitator, thermometer, Dean-Stark trap, and condenser was charged with 230 g of 2-(2,2,3-trimethylcyclopent-3-en-1-yl) acetaldehyde at 86.6% purity (1.31 moles), 250 g of 2-methyl-3-buten-2-ol (2.90 moles), 1000 ml of toluene and 0.4 g of p-TSA. The flask was heated to reflux and 37 ml of a water/alcohol mixture was distilled off after 24 hours. The flask was cooled and the contents were washed with 500 ml of 10% sodium carbonate and 500 ml of brine. The crude product, 354.4 g, was distilled to afford 146 g of purified aldehyde (51% yield). BP 82° C./0.15 mmHg; $^1$H-NMR (300 MHz), δ0.84 (3H, s), 0.96 (3H, s), 1.60 (6H, s), 1.67 (3H, s), 2.0–2.5 (6H, m), 5.05 (1H, br s), 5.25 (1H, s), 9.57 (1H, d, J=5.25 Hz); $^{13}$C-NMR (75 MHz), δ12.58, 17.94, 20.20, 25.83, 26.32, 27.62, 34.04, 47.12, 49.99, 54.74, 120.85, 121.45, 134.16, 149.31, 206.46; IR (Neat), 2980, 1730, 1450, 1370 cm$^{-1}$; MS (m/e), 220 (M$^+$), 205, 108 (Base);

Odor: Fatty fresh aldehyde green muguet

Example 36

2-(2,2,3-Trimethylcyclopent-3-en-1-yl)-5-methyl-4-hexenol (mixture of diastereomers)

Similar to Example 2, 20.3 g of the aldehyde from Example 35 at 80.7% purity (0.074 mole), 1.6 g of sodium borohydride (0.042 mole), 70 ml of ethanol were reacted in the usual way to afford 19.5 g of crude alcohol which was distilled to afford 13.0 g of purified alcohol (79% yield). BP 80° C./0.08 mmHg; $^1$H-NMR (300 MHz), δ0.88 (3H, s), 1.07 (3H, s), 1.60 (3H, s), 1.65 (3H, s), 1.71 (3H, s), 1.5–1.7 (2H, m), 1.8–2.3 (5H, m), 3.65 (2H, m), 5.22 (2H, br s); $^{13}$C-NMR (75 MHz), δ12.66, 17.92, 19.76, 26.02, 27.36, 28.47, 34.05, 42.04, 47.09, 49.83, 64.48, 122.00, 123.28, 133.30, 149.16; IR (Neat), 3350, 2980, 1450, 1370, 1040 cm$^{-1}$; MS (m/e), 222 (M$^+$), 207, 191, 135, 121, 112, 95, 41 (Base);

Odor: Weak floral rosey honey

Example 37

2,2-Dimethyl-5-(2,2,3-trimethylcyclopent-3-en-1-yl)-tetrahydropyran (mixture of diastereomers)

Similar to Example 3, 128 g of the alcohol from Example 36 at 93.7% purity (0.540 mole), 3.5 g of p-TSA, and 400 ml of heptane were refluxed for 120 hours. The usual work-up afforded 135.9 g of crude tetrahydropyran which was distilled to afford 92.7 g of purified product (78% yield). BP 85° C./0.25 mmHg; $^1$H-NMR (300 MHz), δ0.88 (3H, s), 1.02 (3H, s), 1.10 (3H, s), 1.19 (3H, s), 1.57 (3H, s), 1.4–2.3 (8H, m), 3.2–3.9 (2H, m), 5.20 (1H, s); $^{13}$C-NMR (75 MHz), δ12.51, 19.17, 21.68, 25.91, 27.16, 31.08, 33.36, 36.57, 46.73, 48.06, 52.47, 66.60, 70.63, 121.30, 148.65; IR (Neat), 2980, 1450, 1370, 1090 cm$^{-1}$; MS (m/e), 222 (M$^+$), 207, 191, 149, 121, 112, 108, 95, 41 (Base);

Odor: Weak piney

Example 38

2,2-Dimethyl-5-(2,2,3-trimethylcyclopent-1-yl)tetrahydropyran (mixture of diastereomers)

The tetrahydropyran from Example 37, 40.5 g at 91.4% purity (0.166 mole), was hydrogenated in a Parr shaker with 1.0 g of 5% Pd on carbon in 40 ml of ethanol at 35°–45° C. The resultant product, 40.7 g, was distilled to afford 37.3 g of purified product (100% yield). BP 86° C./0.4 mmHg; $^1$H-NMR (300 MHz), δ0.62 (3H, s), 0.78 (3H, d, J=6.72 Hz), 0.90 (3H, s), 0.95–1.05 (2H, m), 1.17 (3H, s), 1.18 (3H, s), 1.2–1.8 (9H, m), 3.2–3.9 (2H, m); $^{13}$C-NMR, δ13.68, 14.34, 21.44, 25.87, 26.61, 27.14, 29.65, 31.20, 36.70, 38.31, 42.42, 45.85, 52.87, 66.36, 70.52; IR (Neat), 2980, 1470, 1370, 1090 cm$^{-1}$; MS (m/e), 224 (M$^+$) 209, 191 123, 109, 95, 69 43 (Base);

Odor: Weak woody

Example 39

[rac]-2,2-Dimethyl-5-(2,3,3-trimethylcyclopent-1-en-1-yl)tetrahydropyran

The tetrahydropyran from Example 37, 38.5 g at 90.8% purity, 250 ml of heptane, and 2.5 g of Amberlyst-15 were refluxed for 4 hours at 95° C. The resultant product, 40 g, was distilled to afford 30 g of purified product (88% yield). BP 80° C./0.45 mmHg; $^1$H-NMR (300 MHz), δ0.95 (6H, s), 1.22 (6H, s), 1.52 (3H, s), 1.5–1.72 (6H, m), 2.1 (2H, m), 2.51 (1H, m), 3.4 (2H$_{AB}$, AB Quartet, J$_{AB}$=11.4 Hz); $^{13}$C-NMR (75 MHz), δ9.33, 21.42, 24.52, 26.28, 26.60, 29.49, 31.37, 36.36, 36.50, 38.85, 46.64, 64.43, 70.72, 133.17, 140.67; IR (Neat), 2980, 1460, 1370, 1085 cm$^{-1}$; MS (m/e), 222 (M$^+$), 207, 191, 121 (Base);

Odor: Weak woody

Example 40

2,2-Dimethyl-5-(2,3,3-trimethylcyclopent-1-yl)-tetrahydropyran (mixture of diastereomers)

The tetrahydropyran from Example 39, 24.6 g at a purity of 77.6% (0.086 mole) was hydrogenated using 2.0 g of 5% Pd on carbon in 50 ml of ethanol at a temperature of 60°–80° C. The resulting crude product, 24.9 g, was distilled to afford 19 g of purified tetrahydropyran (98% yield). BP 82° C./0.3 mmHg; $^1$H-NMR (300 MHz), δ0.74 (3H, s), 0.85 (3H, d, J=6.75 Hz), 0.93 (3H, s), 1.18 (3H, s), 1.20 (3H, s), 1.2–1.8 (11H, m), 3.35–3.7 (2H, m); $^{13}$C-NMR (75 MHz), δ14.04, 14.94, 22.08, 25.44, 26.33, 28.34, 31.08, 36.74, 39.25, 40.23, 40.76, 46.38, 46.94, 66.42, 71.07; IR (Neat), 2980, 1470, 1370, 1090 cm$^{-1}$; MS (m/e), 224 (M$^+$), 209, 191, 151, 135, 123, 110, 95 (Base);

Odor: Weak woody

Example 41

2,5-Dimethyl-2-(2,2,3-trimethylcyclopent-3-en-1-yl-4-hexenal (mixture of diastereomers)

In a procedure similar to Example 35, 2-(2,2,3-trimethylcyclopent-3-en-1-yl)propanal (from Example 5), 115 g at 94% purity (0.65 mole), 125 g of 2-methyl-3-buten-2-ol (1.45 moles), 500 ml of heptane, and 0.55 g of p-TSA were refluxed for 72 hours. A total of 15 ml of an H$_2$O/alcohol mixture was distilled off. A GC sample shows 11% starting material and 83.6% product. After the usual work-up 189.2 g of crude product were obtained. The product was distilled to afford 118 g of purified aldehyde (78% yield). BP 92° C./0.2 mmHg; $^1$H-NMR (300 MHz), δ0.87 (3H, s), 1.05 (3H, s), 1.07 (3H, s), 1.56 (3H, s), 1.61 (3H, s), 1.69 (3H, s), 2.1–2.45 (5H, m), 5.02 (1H, m), 5.28 (1H, s), 9.71 (1H, s); $^{13}$C-NMR (75 MHz), δ12.34, 16.16, 17.95, 22.39, 26.00, 28.03, 30.90, 35.82, 48.14, 52.78, 55.38, 118.80, 121.10, 134.68, 148.07, 206.87; IR (Neat), 2980, 2710, 1720, 1450, 1380; MS (m/e), 234 (M$^+$), 219, 205, 126, 108, 69, 41 (Base);

Odor: Floral quinoline

Example 42

2,5-Dimethyl-2-(2,2,3-trimethylcyclopent-3-en-1-yl)-4-hexenol (mixture of diastereomers)

A 1 liter 4 neck flask fitted with mechanical agitator, nitrogen inlet, 250 ml side arm dropping funnel, thermometer and condenser was charged with 8.0 g of lithium aluminum hydride (0.21 mole) and 500 ml of dry ether. The flask was cooled to 5° C. and 101.3 g of the aldehyde from Example 41 at a purity of 97% (0.419 mole) in 125 ml of dry ether was added dropwise to the flask. After the addition the contents were stirred for 30 minutes at 5° C., then the reaction was quenched at 5° C. by the addition of 16 ml of H$_2$O, then 12.8 ml of 10% sodium hydroxide. The batch was filtered and concentrated in vacuo to afford 100.8 g of crude alcohol. The alcohol was distilled from 1 g of sodium carbonate to afford 98.3 g of purified product (99% yield). BP 114° C./0.3 mmHg; $^1$H-NMR (300 MHz), δ1.00 (6H, s), 1.13 (3H, s), 1.56 (3H, s), 1.56 (3H, s), 1.65 (3H, s), 1.67 (1H, m), 1.72 (3H, s), 2.08 (5H, m), 3.60 (2H$_{AB}$, AB quartet, J$_{AB}$=11.0 Hz), 5.28 (2H, br s); $^{13}$C-NMR (75 MHz), δ12.35, 17.93, 19.45, 22.31, 26.19, 28.32, 30.88, 36.38, 41.96, 48.16, 54.05, 68.87, 120.75, 121.41, 133.52, 148.37; IR (Neat), 3380, 2980, 1450, 1370, 1040 cm$^{-1}$; MS (m/e), 236 (M$^+$), 221, 205, 149, 121, 109 (Base);

Odor: Weak floral

Example 43

2,2,5-Trimethyl-5-(2,2,3-trimethylcyclopent-3-en-1-yl)tetrahydropyran (mixture of diastereomers)

Similar to Example 8, the alcohol from Example 42, 60.3 g at 96.7% purity (0.247 mole), 450 ml of heptane, and 1.5 g of p-TSA were refluxed for 36 hours. The crude product, 64.2 g, was distilled to afford 49 g of purified tetrahydropyran (84% yield). BP 90° C./0.3 mmHg; $^1$H-NMR (300 MHz), δ0.88 (3H, s), 0.98 (3H, s), 1.12 (3H, s), 1.18 (3H, s), 1.21 (3H, s), 1.55 (3H, s), 1.4–2.2 (7H, m), 3.2–3.7 (2H, m), 5.3 (1H, m); $^{13}$C-NMR (75 MHz), δ12.28, 19.17, 22.22, 23.37, 27.53, 30.31, 32.33, 35.79, 38.74, 45.36, 50.66, 56.84, 70.14, 71.54, 121.26, 148.40; IR (Neat), 2980, 1455, 1370, 1075 cm$^{-1}$; MS (m/e), 236 (M$^+$), 221, 205, 193, 149, 135, 126, 108 (Base);

Odor: Fresh spicy ginger milky green nootkatone

Example 44

2-(3,3-Dimethylbicyclo[2.2.1]hept-2-yl)-4-methyl-4-pentenal (mixture of diastereomers)

In a similar procedure as in Example 1, 247 g of 3,3-dimethylbicyclo[2.2.1]hept-2-yl acetaldehyde at 93.3% purity (1.39 moles), 220 g of methallyl alcohol (3.0 moles), 800 ml of heptane and 1.0 g of p-TSA were refluxed for 16 hours while collecting 29.5 ml of water/alcohol mixture. The usual work-up afforded 414.7 g of crude acetal. BP 118° C./0.3 mmHg; $^1$H-NMR (300 MHz), δ0.81 (3H, s), 0.94 (3H, s), 0.98–1.7 (11H, m), 1.76 (6H, s), 3.96 (4H, m), 4.55 (1H, m), 4.88 (2H, s), 4.99 (2H, s); $^{13}$C-NMR (75 MHz), δ19.78, 21.86, 24.75, 27.82, 30.23, 32.29, 35.81, 37.12, 41.43, 45.89, 49.02, 68.81, 102.21, 111.86, 142.29; IR (Neat), 2980, 1660, 1460, 1370, 1130, 1030, 900 cm$^{-1}$; MS (m/e), 221 (M$^+$-71), 155, 109, 55 (Base);

Odor: Weak

The crude acetal, 364.4 g, was heated with 2.0 g of citric acid at about 120 mmHg to a maximum temperature of 168° C. Methallyl alcohol, 78.7 g, was collected. When the distillation ends the reaction was heated for 2 hours at 160° C. The batch was cooled and washed with water, 10% sodium carbonate and brine. The crude aldehyde, 285 g, was distilled to afford 152 g of purified product (56% yield). BP 88° C./0.3 mmHg; $^1$H-NMR (300 MHz), δ0.86 (3H, s), 0.99 (3H, s), 1.25 (2H, m), 1.5–1.8 (6H, m), 1.73 (3H, s), 2.1–2.4 (4H, m), 4.67 (1H, s), 4.75 (1H, s), 9.54 (1H, d, J=4.32 Hz); $^{13}$C-NMR (75 MHz), δ20.49, 22.46, 24.66, 26.19, 27.91, 32.24, 36.30, 38.49, 40.22, 48.18, 50.06, 54.55, 112.81, 142.25, 205.39; IR (Neat), 2980, 2700, 1730, 900 cm$^{-1}$; MS (m/e), 220 (M$^+$), 205, 191, 177, 164, 151, 136, 121,109, 41 (Base);

Odor: Fruity

Example 45

2-(3,3-Dimethylbicyclo[2.2.1]hept-2-yl)-4-methyl-4-pentenol (mixture of diastereomers)

Similar to Example 7, 82.7 g of the aldehyde from Example 44 at a purity of 86% (0.32 mole), 44.2 g of aluminum isopropoxide (0.22 mole) and 155 g of isopropanol were reacted to afford 81.3 g of crude alcohol. The product was distilled from 1 g of soda ash to afford 61 g (85% yield) of purified alcohol. BP 97° C./0.2 mmHg; $^1$H-NMR (300 MHz), δ0.97 (3H, s), 1.01 (3H, s), 1.1–1.3 (4H, m), 1.6–1.8 (5H, m), 1.81 (3H, s), 1.9–2.3 (4H, m), 3.4–3.7 (2H, m), 4.78 (1H, s), 4.84 (1H, s); $^{13}$C-NMR (75 MHz), δ20.16, 21.82, 22.51, 23.82, 25.16, 28.88, 31.18, 36.24, 39.72, 40.62, 50.45, 54.60, 65.81, 111.83, 146.78; IR (Neat), 3390, 2960, 1650, 1460, 1370, 1050, 1040 cm$^{-1}$; MS (m/e), 207 (M$^+$-15), 191, 166, 148, 135, 122, 107, 93, 81, 67, 55, 41 (Base);

Odor: Weak

Example 46

2,2-Dimethyl-4-(3,3-dimethylbicyclo[2.2.1]hept-2-yl)-tetrahydrofuran (mixture of diastereomers)

Similar to Example 4, the alcohol from Example 45, 40.4 g, at a purity of 92.3% (0.168 mole), was refluxed for about 1 hour with 1.0 g of Amberlyst-15 in 150 ml of hexane. After the usual work-up 39.4 g of crude product was obtained. This material was distilled to afford 35.4 g of purified product (95% yield). BP 86° C./0.4 mmHg; $^1$H-NMR (300 MHz), δ0.86 (3H, s), 0.92 (3H, s), 1.1–1.4 (5H, m), 1.19 (3H, s), 1.27 (3H, s), 1.6–2.5 (7H, m), 3.4 (1H, m), 4.02 (1H, m); $^{13}$C-NMR (75 MHz), δ21.17, 22.57, 25.17, 28.31, 29.20, 30.78, 33.37, 38.93, 43.35, 46.04, 50.29, 56.30, 60.83, 72.74, 80.23; IR (Neat), 2980, 1460, 1370, 1110 cm$^{-1}$; MS (m/e), 222 (M$^+$), 207 (Base), 149, 109;

Odor: Woody amber

Example 47

3-(3,3-Dimethylbicyclo[2.2.1]hept-2-yl-5-methyl-5-hexen-2-ol (mixture of diastereomers)

Similar to Example 11, 35.0 g of the aldehyde from Example 44 at a purity of 90.5% (0.143 mole), 66 ml of 3.0M methylmagnesium bromide in 250 ml of dry ether afforded 34.4 g of crude alcohol. This alcohol was distilled from 1 g of soda ash to afford 21 g of purified product (62% yield); BP 97° C./0.1 mmHg; $^1$H-NMR (300 MHz), δ1.03 (3H, s), 1.05 (3H, s), 1.08–1.17 (4H, m), 1.23 (3H, d, J=6.84 Hz), 1.60–1.87 (7H, m), 1.79 (3H, s), 2.0–2.3 (2H, m), 3.86 (1H, q, J=6.66 Hz), 4.76 (1H, s), 4.80 (1H, s); $^{13}$C-NMR (75 MHz) consistent with assigned structures; IR (Neat) 3400, 2970, 1650, 1470, 1370, 1130, 1080, 1050, 890 cm$^{-1}$; MS (m/e,), 221 (M$^+$-15), 203, 192, 177, 163, 149, 108 (Base), 43;

Odor: Weak

Example 48

2,2,5-Trimethyl-4-(3,3-bicyclo[2.2.1]hept-2-yl)tetrahydrofuran (mixture of diastereomers)

Similar to Example 4, 19.1 g of the alcohol from Example 47 at 100% purity (0.08 mole), 80 ml of heptane, and 1.0 g of Amberlyst-15 were refluxed for 2 hours. After the usual work-up 20.3 g of crude tetrahydrofuran was distilled to afford 16.8 g of purified product (88% yield). BP 65° C./0.04 mmHg; $^1$H-NMR (300 MHz), spectra consistent with assigned structures; $^{13}$C-NMR (75 MHz), spectra consistent with assigned structures; IR (Neat), 2980, 1465, 1370, 1090 cm$^{-1}$; MS (m/e), 221 (M$^+$-15), 203, 192, 177, 163, 149, 136, 123, 108 (Base), 93, 81, 67, 43;

Odor: Amber dry tobacco

Example 49

2-(3,3-Dimethylbicyclo[2.2.1]hept-2-yl)propenal (mixture of diastereomers)

A 4 neck 3 liter bottom drain flask equipped with condenser, nitrogen inlet, mechanical agitator, thermometer and 60 ml side arm dropping funnel was charged with 1044 g of 3,3dimethylbicyclo[2.2.1]hept-2-yl acetaldehyde (6.02 moles), 533 g of 37% formaldehyde (6.57 moles) and 2.2 g of BHT. The contents were brought to reflux (98° C.) and 25.9 g of diethylamine (0.35 mole) were added over 15 minutes. The batch was refluxed for 18.5 hours. The flask was brought to 60° C. and 65 g of 37% formaldehyde (0.80 mole) and 12.7 g of diethylamine (0.17 mole) were added and reflux was continued for 5 hours. The flask was cooled and the oil layer was separated from the aqueous layer. The oil was washed with 36 g of acetic acid (0.6 mole) for 10 minutes, then 300 ml of brine was added and stirring continued for 5 minutes. Then 300 ml of heptane was added and the batch was stirred for 5 minutes. The top organic layer was washed with 400 ml of a 1:1 mixture of 10% sodium carbonate and brine. The organic layer was washed with 500 ml of brine. All the aqueous washings were back extracted with 300 ml of heptane. The organic washings were dried, filtered and concentrated in vacuo to afford 1148 g of crude product. The aldehyde was distilled to afford 810 g of purified product (72% yield). BP 95° C./2.2 mmHg; $^1$H-NMR (300 MHz), δ0.61 (3H, s), 1.17 (3H, s), 1.2–1.75 (7H, m), 2.20 (2H, m), 5.98 (1H, s), 6.30 (1H, s), 9.51 (1H, s); $^{13}$C-NMR (75 MHz), δ21.47, 24.23, 26.22, 29.94, 36.95, 41.53, 42.26, 49.35, 51.25, 132.54, 153.05, 195.62; IR (Neat), 2980, 2810, 2760, 2700, 1690, 1470, 1370 cm$^{-1}$; MS (m/e), 178 (M$^+$), 163, 145, 135, 107, 79, 67, 41 (Base);

Odor: Borneol camphor

Example 50

2-(3,3-Dimethylbicyclo[2.2.1]hept-2-yl)propanal (mixture of diastereomers)

The crude aldehyde from Example 49, 271.5 g at 85% purity (1.29 moles) was hydrogenated on a Parr shaker using 5.0 g of 5% Pd on carbon and 5.0 g of sodium carbonate. In this way 254.6 g of crude propanal were obtained. The batch was distilled to afford 176.7 g of purified product (66% yield); BP 50° C./0.08 mmHg; $^1$H-NMR (300 MHz), δ1.03 (6H, s), 1.09 (3H, d, J=6.42 Hz), 1.2–1.7 (9H, m), 2.36 (1H, m), 9.50 (1H, d, J=4.53 Hz); $^{13}$C-NMR (75 MHz), δ13.98, 15.45, 21.95, 23.90, 26.12, 28.68, 30.61, 36.15, 41.62, 49.88, 56.07, 204.80; IR (Neat), 2980, 2700, 1730, 1470, 1370 cm$^{-1}$; MS (m/e), 180 (M$^+$), 165, 151, 122, 109, 95, 41 (Base);

Odor: Camphor medicinal

Example 51

2,4-Dimethyl-2-(3,3-dimethylbicyclo[2.2.1]hept-2-yl)-4-pentenal (mixture of diastereomers)

Similar to Example 6, 80.0 g of the aldehyde in Example 50, at a purity of 93.6% (0.46 mole) in 40 ml of DMF, 60 g of potassium t-butoxide (0.51 mole) in 250 ml of DMF, and 60 g of methallyl chloride (0.63 mole) in 40 ml of DMF, were reacted in the usual way to afford 97.9 g of crude C-alkylate and O-alkylate (approximately 1:1). The mixture was heated at 165°–175° C. for 2 hours to afford 93.9 g of crude product. This product was distilled to afford 85.9 g of purified aldehyde (83% yield). BP 90° C./0.15 mmHg; $^1$H-NMR (300 MHz), δ1.05 (6H, s), 1.11 (3H, s), 1.13–1.3 (3H, m), 1.5–2.7 (5H, m), 1.61 (3H, s), 2.19–2.55 (3H, m), 4.66 (1H, s), 4.84 (1H, s), 9.74 (1H, s); $^{13}$C-NMR (75 MHz), δ15.45, 23.81, 26.41, 29.46, 31.93, 34.21, 37.30, 40.31, 43.84, 47.74, 50.06, 53.45, 59.85, 115.85, 141.38, 207.52; IR (Neat), 2980, 2700, 1725, 1650, 1470, 1370, 895 cm$^{-1}$; MS (m/e), 219 (M$^+$-15), 191, 178, 149, 135, 123, 109, 95 (Base);

Odor: Woody amber

Example 52

2,4-Dimethyl-2-(3,3-dimethylbicyclo[2.2.1]hept-2-yl-4-pentenol (mixture of diastereomers)

Similar to Example 2, 63.4 g of the aldehyde from Example 51 at a purity of 98% (0.265 mole), 6.0 g of sodium borohydride (0.158 mole), and 200 ml of ethanol were reacted in the usual way. The crude alcohol, 62.6 g, was distilled to afford 41 g of product (65% yield). BP 92° C./0.1 mmHg; $^1$H-NMR (300 MHz), δ1.03 (3H, s), 1.10 (3H, s), 1.17 (3H, s), 1.1–1.3 (2H, m), 1.3–1.7 (7H, m), 1.83 (3H, s), 2.1–2.4 (3H, m), 3.4–3.65 (2H, m), 4.75 (1H, s), 4.87 (1H, s); $^{13}$C-NMR (75 MHz), δ20.08, 23.37, 25.45, 26.80, 26.91, 29.61, 32.73, 37.46, 40.09, 43.21, 44.43, 51.09, 59.37, 69.19, 114.71, 144.70; IR (Neat), 3400, 2980, 1640, 1470, 1370, 1040, 890 cm$^{-1}$; MS (m/e), 221 (M$^+$-15), 205, 181, 163, 149, 135, 123, 107, 93, 81, 67, 55, 41 (Base);

Odor: Weak

Example 53

2,2,4-Trimethyl-4-(3,3-dimethylbicyclo[2.2.1]hept-2-yl)tetrahydrofuran (mixture of diastereomers)

Similar to Example 4, 33.4 g of the alcohol from Example 52 at a purity of 96.8% (0.136 mole), 0.5 g of Amberlyst-15 and 150 ml of heptane were refluxed for 12 hours. After the usual work-up, 35.6 g of crude tetrahydrofuran was distilled to afford 31.8 g of purified product (98% yield). BP 75° C./0.08 mmHg; $^1$H-NMR (300 MHz), δ1.01 (3H, s), 1.05 (3H, s), 1.21 (3H, s), 1.24 (3H, s), 1.31 (3H, s), 1.1–1.3 (2H, m), 1.35–2.05 (9H, m), 3.58 (2H, m); $^{13}$C-NMR (75 MHz), δ23.67, 26.36, 26.63, 28.04, 29.24, 29.41, 32.22, 37.19, 41.65, 43.64, 48.23, 50.08, 58.60, 63.23, 77.49, 80.10; IR (Neat), 2980, 1460, 1370, 1060 cm$^{-1}$; MS (m/e), 236 (M$^+$), 221, 205, 193, 163, 149, 135, 125, 109, 43 (Base);

Odor: Woody amber

Example 54

2-Methyl-2-(3,3-dimethylbicyclo[2.2.1]hept-2-yl)-4-pentenal (mixture of diastereomers)

Similar to Example 6, 330.3 g of the aldehyde from Example 50, at a purity of 92.3% (1.69 moles) in 160 ml of DMF, 223.9 g of potassium t-butoxide (1.89 moles) in 1000 ml of DMF, and 165.8 g of allyl chloride (2.12 moles) in 160 ml of DMF were reacted in the usual manner to afford 401.9 g of crude C-and O-alkylate. This material was heated under nitrogen at 165° C. for 2.5 hours to afford the crude C-alkylate which was distilled to afford 364.2 g of purified aldehyde (81% yield). BP 95° C./0.15 mmHg; $^1$H-NMR (300 MHz), δ0.93 (3H, s), 1.06 (3H, s), 1.11 (3H, s), 1.1–1.7 (8H, m), 2.2–2.5 (3H, m), 5.05 (2H, m), 5.6 (1H, m), 9.64 (1H, s); $^{13}$C-NMR (75 MHz), δ16.18, 23.15, 26.26, 29.33, 31.97, 33.95, 37.95, 39.94, 43.08, 49.93, 52.97, 59.35, 118.00, 133.29, 206.70; IR (Neat), 2980, 2700, 1725, 1640, 1470, 1370, 920 cm$^{-1}$; MS (m/e), 220 (M$^+$), 205, 179, 161, 135, 121, 109, 95, 81, 41 (Base);

Odor: Woody amber

Example 55

2-Methyl-2-(3,3-dimethylbicyclo[2.2.1]hept-2-yl)-4-pentenol (mixture of diastereomers)

Similar to Example 2, 58.8 g of the aldehyde from Example 54, at a purity of 97.5% (0.260 mole), 4.0 g of sodium borohydride (0.105 mole), and 175 ml of ethanol were reacted in the usual way to afford 59.5 g of crude alcohol. The alcohol was distilled to afford 49.7 g of purified product (86% yield). BP 97° C./0.15 mmHg; $^1$H-NMR (300 MHz), δ0.96 (3H, s), 1.12 (3H, s), 1.17 (3H, s), 1.2–1.8 (8H, m), 2.1–2.24 (4H, m), 3.52 (2H, br s), 5.06 (2H, m), 5.9 (1H, m); $^{13}$C-NMR (300 MHz), δ19.39, 23.37, 26.96, 29.44, 32.71, 37.43, 39.79, 41.49, 42.78, 44.31, 51.05, 58.20, 68.71, 117.12, 136.10; IR (Neat), 3400, 2980, 1640, 1470, 1370, 1040, 910 cm$^{-1}$; MS (m/e), 222 (M$^+$), 207, 191,181, 163, 135, 123, 107, 81, 67 (Base);

Odor: Weak woody

Example 56

2,4-Dimethyl-4-(3,3-dimethylbicyclo[2.2.1]hept-2-yl)-tetrahydrofuran (mixture of diastereomers)

Similar to Example 4, 31.4 g of the alcohol from Example 55 at a purity of 100% (0.141 mole), 1.0 g of Amberlyst-15, and 150 ml of heptane were refluxed for about 16 hours. After the usual work-up, the crude tetrahydrofuran, 34.1 g, was distilled to afford 29.4 g of purified product (93.6% yield). BP 70° C./0.04 mmHg; $^1$H-NMR (300 MHz), δ1.00 (3H, s), 1.06 (3H, s), 1.13 (3H, s), 1.22 (3H, d, J=6.03 Hz), 1.0–1.4 (4H, m), 1.5–2.3 (7H, m), 3.4–4.1 (3H, m); $^{13}$C-NMR (75 MHz), δ20.92, 22.52, 23.68, 26.35, 29.72, 31.97, 34.74, 37.23, 41.69, 43.37, 49.96, 50.10, 63.28, 74.00, 79.07; IR (Neat), 2980, 1470, 1370, 1080, 1055, 1050 cm$^{-1}$; MS (m/e), 222 (M$^+$), 207, 189, 179, 161, 135, 109 (Base);

Odor: Woody amber

Example 57

2-(6,6-Dimethylbicyclo[3.1.1]hept-2-yl)propenal (mixture of diastereomers)

In a similar manner to Example 49, 342 g of 6,6-dimethylbicyclo[3.1.1]hept-2-yl acetaldehyde at a purity of 97% (1.99 moles), 178 g of 37% formaldehyde (2.2 moles), 7.3 g of diethylamine (0.1 mole), and 0.8 g of BHT were refluxed for 1.5 hours. After the usual work-up, 370 g of crude propenal was distilled to afford 317 g of purified product (89% yield). BP 75° C./0.5 mmHg; $^1$H-NMR (300 MHz), δ0.92 (3H, s), 1.23 (3H, s), 1.47–2.40 (8H, m), 3.1 (1H, t, J=8.91 Hz), 5.91 (1H, s), 6.20 (1H, s), 9.50 (1H, s); $^{13}$C-NMR (75 MHz), δ20.06, 20.92, 23.88, 26.76, 28.03, 32.82, 40.08, 41.32, 44.34, 131.53, 155.46, 194.97; IR (Neat), 2960, 2700, 1690, 940 cm$^{-1}$; MS (m/e), 177 (M$^+$-1), 163, 145, 135, 121,107, 91, 79, 41 (Base);

Odor: Piney camphoraceous

Example 58

2-(6,6-Dimethylbicyclo[3.1.1]hept-2-yl)propanal (mixture of diastereomers)

281 g of the propenal in Example 57 (1.53 moles) were hydrogenated on a Parr shaker with 2.7 g of 5% Pd on carbon. The resulting propanal, 282 g, was distilled to afford 242 g of purified product (87% yield). BP 64° C./0.4 mmHg; $^1$H-NMR (300 MHz), δ0.95 (3H, s), 1.02 (3H, s), 1.20 (3H, d, J=7.62 Hz), 1.30–2.50 (10H, m), 9.62 (1H, d, J=2.55 Hz); $^{13}$C-NMR NMR (75 MHz), δ11.29, 20.16, 23.47, 24.39, 26.84, 27.95, 36.31, 40.33, 42.72, 44.16, 51.68, 205.56; IR (Neat) 2960, 2700, 1735, 1470, 1370; MS (m/e), 165 (M$^+$-15), 149, 137, 122, 107, 95, 79, 69, 55, 41 (Base);

Odor: Camphoraceous piney fruity

Example 59

2-(6,6-Dimethylbicyclo[3.1.1]hept-2-yl)-4-methyl-4-pentenal (mixture of diastereomers)

In a manner similar to Example 6, 90 g of 6,6-dimethylbicyclo[3.1.1]hept-2-yl acetaldehyde (0.529 mole) in 40 ml of DMF, 108 g of potassium t-butoxide (0.91 mole) in 400 ml of DMF, and 93 g of methallyl chloride (1.02 moles) in 40 ml of DMF were reacted in the usual manner. After work-up the crude mixture of C- and O-alkylates, 112 g, was heated at 165°–175° C. for 4 hours. The crude product was dwastilled to afford 34.5 g of purified product (30% yield). BP 90° C./0.1 mmHg; $^1$H-NMR (300 MHz), δ1.06 (3H, s), 1.16 (3H, s), 1.69 (3H, s), 1.3–2.6 (12H, m), 4.67 (1H, s), 4.74 (1H, s), 9.36 (1H, m); $^{13}$C-NMR (75 MHz), spectra consistent with assigned structures; IR (Neat) 2960, 2700, 1730, 1650, 1470, 1370, 890 cm$^{-1}$; MS (m/e), 220 (M$^+$), 205, 189, 177, 163, 149, 135, 121,107, 93, 79, 69, 41 (Base);

Odor: Fruity raspberry sweet

Example 60

2-(6,6-Dimethylbicyclo[3.1.1]hept-2-yl)-4-methyl-4-pentenol (mixture of diastereomers)

In a reduction similar to Example 42, the aldehyde from Example 59, 21.5 g (0.091 mole), was added dropwwase to 1.78 g of lithium aluminum hydride (0.046 mole) in 100 ml of dry ether at 0° C. After quenching with 3.6 ml of water and 2.8 ml of 10% sodium hydroxide, 21.4 g of crude alcohol were obtained (100% yield). BP 110°–120° C./0.1 mmHg; $^1$H-NMR (300 MHz), δ1.02 (3H, s), 1.21 (3H, s), 1.73 (3H, s), 1.5–2.3 (12H, m), 3.02 (2H, m), 4.78 (2H, m); $^{13}$C-NMR (75 MHz), spectra consistent with assigned structures; IR (Neat), 3350, 2940, 1650, 1470, 1370, 890 cm$^{-1}$; MS (m/e), 222 (M$^+$), 207, 191, 179, 161,149, 135, 123, 107, 93, 81, 69 (Base);

Odor: Weak

Example 61

2,2-Dimethyl-4-(6,6-dimethylbicyclo[3.1.1]hept-2-yl)-tetrahydrofuran (mixture of diastereomers)

In a procedure similar to Example 4, 20 g of the alcohol from Example 60 at a purity of 85% (0.076 mole), 1.25 g of Amberlyst-15, and 70 ml of heptane were refluxed for 24 hours. After the usual work-up the crude tetrahydrofuran, 19.6 g, was distilled to afford 15 g of purified product (88% yield). BP 55° C./0.05 mmHg; $^1$H-NMR (300 MHz), δ1.05 (3H, s), 1.18 (6H, s), 1.26 (3H, s), 1.5–2.5 (12H, m), 3.36 (1H, m), 3.93 (1H, m); $^{13}$C-NMR (75 MHz), δ20.06, 21.47, 23.34, 26.41, 28.12, 28.87, 33.46, 39.70, 40.65, 41.43, 44.83, 45.04, 46.30, 71.94, 80.64; IR (Neat), 2960, 1470, 1370, 1050 cm$^{-1}$; MS (m/e), 222 (M$^+$), 207, 191,165, 149, 137, 123, 107, 69, 43 (Base);

Odor: Woody fruity

Example 62

2-(6,6-Dimethylbicyclo[3.1.1]hept-2-yl)-4-pentenal (mixture of diastereomers)

In a procedure similar to Example 6, 100 g of 6,6-dimethylbicyclo[3.1.1]hept-2-yl acetaldehyde at a purity of 98.3% (0.59 mole) in 50 ml of DMF, 82 g of potassium t-butoxide (0.69 mole) in 300 ml of DMF, and 55 g of allyl chloride in 50 ml of DMF (0.78 mole) were reacted in the usual way to afford 110.5 g of crude product composed of 36% starting material, 31% O-alkylate and 21% C-alkylate. The product was heated at 165°–185° C. for 6 hours. The crude aldehyde, 105.6 g, was distilled to afford 21.4 g of purified product (17% yield). A major impurity in the crude was the dialkylation product. BP product 114° C./1.2 mmHg; $^1$H-NMR (300 MHz), δ1.05 (3H, s), 1.21 (3H, s), 1.3–2.6 (12H, m), 5.01 (2H, m), 5.7 (1H, m), 9.47 (1H, m); $^{13}$C-NMR (75 MHz), spectra consistent with assigned structures; IR (Neat), 2970, 2700, 1730, 1640, 1450, 1370, 910 cm$^{-1}$; MS (m/e), 205 (M$^+$-1), 191, 175, 163, 122, 107, 93, 41 (Base);

Odor: Berry butyric

Example 63

2-(6,6-Dimethylbicyclo[3.1.1]hept-2-yl)-4-pentenol (mixture of diastereomers)

In a reaction similar to Example 42, 18.9 g of the aldehyde from Example 62 at a purity of 81% (0.074 mole), 1.70 g of lithium aluminum hydride (0.044 mole) in 40 ml of dry ether, were reacted to produce 18.7 g of crude alcohol. A sample was flash distilled. BP 110°–120° C./0.1 mmHg; $^1$H-NMR (300 MHz), spectra consistent with assigned structures; $^{13}$C-NMR (75 MHz), spectra consistent with assigned structures; IR (Neat), 3320, 2960, 1640, 1370, 1420, 1020, 910 cm$^{-1}$; MS (m/e), 193 (M$^+$-15), 177, 163, 147, 123, 107, 93, 81, 67, 41 (Base).

Example 64

2-Methyl-4-(6,6-dimethylbicyclo[3.1.1]hept-2-yl)-tetrahydrofuran (mixture of diastereomers)

Similar to Example 4, 17.1 g of the alcohol from Example 63 at a purity of 80% (0.065 mole), 2.0 g of Amberlyst-15, and 70 ml of heptane were refluxed for 3 hours. The resulting 16.7 g of crude tetrahydrofuran were distilled to afford 13.1 g of purified product (95% yield). BP 72° C./0.05 mmHg; $^1$H-NMR (300 MHz) spectra consistent with assigned structures; $^{13}$C-NMR (75 MHz) spectra consistent with assigned structures; IR (Neat), 2960, 1470, 1370, 1100, 1040 cm$^{-1}$; MS (m/e), 193 (M$^+$-15), 175, 161, 151, 123, 107, 95, 83, 41 (Base);

Odor: Woody amber weak fruity

Example 65

2,4-Dimethyl-2-(6,6-dimethylbicyclo[3.1.1]hept-2-yl)-4-pentenal (mixture of diastereomers)

In a similar manner to Example 6, 100 g of the aldehyde from Example 58 at a purity of 85% (0.47 mole) in 75 ml of DMF, 82 g of potassium t-butoxide (0.69 mole) in 500 ml of DMF, and 78 g of methallyl chloride (0.86 mole) in 50 ml of DMF were reacted in the usual way. In this way 116.2 g of crude O- and C-alkylates (58.1:33.8) were obtained. The crude product was heated at 165°–170° C. for 2 hours. The crude aldehyde was distilled to afford 94.1 g of purified product (85% yield). BP 85° C./0.05 mmHg; $^1$H-NMR (300 MHz), δ0.95 (3H, s), 0.96 (3H, s), 1.18 (3H, s), 1.2–1.4 (2H, m), 1.59 (3H, s), 1.7–2.5 (9H, m), 4.64 (1H, s), 4.80 (1H, s), 9.57 (1H, s); $^{13}$C-NMR (75 MHz), spectra consistent with assigned structures; IR (Neat), 2960, 2700, 1725, 1645, 1470, 1370, 895 cm$^{-1}$; MS (m/e), 234 (M$^+$), 219, 203, 191, 177, 163, 151, 135, 123, 109, 97, 81, 41 (Base);

Odor: Weak

Example 66

2-Methyl-2-(6,6-dimethylbicyclo[3.1.1]hept-2-yl)-4-pentenal (mixture of diastereomers)

In a similar manner to Example 6, 100 g of the aldehyde from Example 58 at a purity of 85% (0.47 mole) in 75 ml of DMF, 90 g of potassium t-butoxide (0.76 mole) in 500 ml of DMF, and 61.5 g of allyl chloride (0.80 mole) in 50 ml of DMF were reacted in the usual way. In this manner 111.4 g of crude O- and C-alkylates (25:55) were obtained. The crude product was heated at 165°–170° C. for 1 hour affording 108 g of crude aldehyde. This material was distilled to afford 85.5 g of purified product (84% yield). BP 79° C./0.15 mmHg; $^1$H-NMR (300 MHz), δ0.94 (3H, s), 0.99 (3H, s), 1.19 (3H, s), 1.3–2.5 (11H, m), 5.02 (2H, m), 5.62 (1H, m), 9.48 (1H, s); $^{13}$C-NMR (75 MHz), spectra consistent with assigned structures; IR (Neat), 2960, 2710, 1725, 1640, 1470, 1370, 920 cm$^{-1}$; MS (m/e), 220 (M$^+$), 205, 189, 179, 123, 107, 95, 81, 69, 41 (Base);

Odor: Woody

Example 67

2,4-Dimethyl-2-(6,6-dimethylbicyclo[3.1.1]hept-2-yl)-4-pentenol (mixture of diastereomers)

Similar to Example 7, 60 g of the aldehyde from Example 65 at a purity of 97.5% (0.25 mole), 125 ml of isopropanol and 30 g of aluminum isopropoxide were refluxed for 1 hour. The usual work up afforded 59.9 g of crude alcohol. The crude alcohol was distilled to afford 52.1 g of purified product (88% yield). BP 103° C./0.09 mmHg; $^1$H-NMR (300 MHz), δ0.82 (3H, s), 0.83 (3H, s), 1.22 (3H, s), 1.79 (3H, s), 1.35–1.8 (1.9–2.2 (6H, m), 3.43 (2H, m), 4.72 (1H, s), 4.87 (1H, s); $^{13}$C-NMR (75 MHz), spectra consistent with assigned structures; IR (Neat), 3400, 2960, 1640, 1470, 1370, 1030, 890 cm$^{-1}$; MS (m/e), 236 (M$^+$), 221, 205, 149, 135, 123, 107, 95, 81, 69, 41 (Base);

Odor: Weak

Example 68

2-Methyl-2-(6,6-dimethylbicyclo[3.1.1]hept-2-yl)-4-pentenol (mixture of diastereomers)

Similar to Example 7, 60 g of the aldehyde from Example 66 at a purity of 96% (0.26 mole), 125 ml of isopropanol and 32 g of aluminum isopropoxide (0.148 mole) were refluxed for 1 hour. The usual work-up afforded 59.9 g of crude alcohol. The crude alcohol was distilled to afford 52.0 g of purified product (89% yield). BP 92° C./0.05 mmHg; $^1$H-NMR (300 MHz), δ0.78 (3H, s), 0.81 (3H, s), 1.21 (3H, s), 1.38–2.50 (12H, m), 3.41 (2H, m), 5.02 (2H, m), 5.87 (1H, m); $^{13}$C-NMR (75 MHz), δ16.27, 18.12, 20.14, 24.39, 25.27, 27.05, 29.27, 37.98, 39.65, 40.81, 43.37, 47.12, 67.62, 117.04, 135.88; IR (Neat), 3380, 2970, 1640, 1470, 1370:, 1040, 910 cm$^{-1}$; MS (m/e), 222 (M$^+$), 207, 191, 161, 135, 123, 107, 93, 81, 67, 41 (Base);

Odor: Weak

Example 69

2,2,4-Trimethyl-4-(6,6-dimethylbicyclo[3.1.1]hept-2-yl)tetrahydrofuran (mixture of diasteromers)

Similar to Example 4, 45.1 g of the alcohol from Example 67 at a purity of 98.5% (0.188 mole), 1.0 g of Amberlyst-15 and 150 ml of heptane were refluxed for 24 hours. After the usual work-up 47.7 g of crude tetrahydrofuran were obtained. The crude was distilled to obtain 41 g of purified product (92% yield). BP 77° C./0.09 mmHg; $^1$H-NMR (300 MHz), δ0.81 (3H, s), 1.02 (3H, s), 1.20 (6H, s), 1.29 (3H, s), 1.41–2.1 (11H, m), 3.48 (2H, m); $^{13}$C-NMR (75 MHz), spectra consistent with assigned structures; IR (Neat), 2980, 1470, 1370, 1050 cm$^{-1}$; MS (m/e), 236 (M$^+$), 221, 163, 135, 123, 112, 107, 43 (Base);

Odor: Woody sandalwood

Example 70

2,4-Dimethyl-4-(6,6-dimethylbicyclo[3.1.1]hept-2-yl)tetrahydrofuran (mixture of diastereomers)

Similar to Example 4, 45.5 g of the alcohol from Example 68 at a purity of 98.2% (0.20 mole), 1.25 g of Amberlyst-15, and 150 ml of heptane were refluxed for 24 hours. After the usual work-up, 45.9 g of crude tetrahydrofuran were obtained. The crude was distilled to obtain 38.5 g of purified product (86% yield). BP 79° C./0.2 mmHg; $^1$H-NMR (300 MHz), spectra consistent with assigned structures; $^{13}$C-NMR (75 MHz), spectra consistent with assigned structures; IR (Neat), 2970, 1470, 1370, 1080, 1040 cm$^{-1}$; MS (m/e), 222 (M$^+$), 207, 164, 149, 135, 123, 107, 98, 81, 69, 43 (Base);

Odor: Woody powdery amber

Example 71

[rac]-2-Methylene-3,5,5-trimethylhexanal

In a similar manner to Example 49, 300 g of 3,5,5-trimethylhexanal at a purity of 95.7% (2.02 moles), 178.4 g of 37% formaldehyde (2.20 moles), 7.3 g of diethylamine (0.1 mole), and 0.8 g of BHT were refluxed for 1.5 hours. After the usual work-up 323.4 g of crude propenal were distilled to afford 267.3 g of purified product (84% yield). BP 45° C./3 mmHg; $^1$H-NMR (300 MHz), δ0.86 (9H, s), 1.06 (3H, d, J=6.9 Hz), 1.29 (1H, dd, J=14.0, 5.07 Hz), 1.58 (1H, dd, J=14.0, 6.9 Hz), 2.85 (1H, m), 5.96 (1H, s), 6.28 (1H, s), 9.52 (1H, s); $^{13}$C-NMR (75 MHz), δ23.34, 27.89, 30.02, 31.32, 49.85, 133.09, 157.60, 194.42; IR (Neat), 2980, 2700, 1695, 940 cm$^{-1}$; MS (m/e), 139 (M$^+$-15), 121, 97, 83, 69, 57 (Base);

Odor: Minty camphor

Example 72

2,3,5,5-Tetramethylhexanal (mixture of diastereomers)

235 g of the propenal from Example 71 (1.48 moles) were hydrogenated on a Parr shaker with 2.5 g of 5% Pd on carbon. The resulting propanal, 231.8 g, was distilled to afford 221.7 g of purified product (96% yield). BP 59° C./5 mmHg; $^1$H-NMR (300 MHz), spectra consistent with assigned structures; $^{13}$C-NMR (75 MHz), spectra consistent with assigned structures; IR (Neat), 2980, 2700, 1730, 1480, 1370; MS (m/e), 141 (M$^+$-15), 123, 98, 83, 57 (Base);

Odor: Fresh citrus chlorine

Example 73

2,4-Dimethyl-2-(4,4-dimethylpent-2-yl)-4-pentenal (mixture of diastereomers)

In a similar manner to Example 6, 100 g of the aldehyde from Example 72 at a purity of 96.1% (0.616 mole) in 50 ml of DMF, 90 g of potassium t-butoxide (0.76 mole) in 500 ml of DMF, and 78 g of methallyl chloride (0.86 mole) in 50 ml of DMF were reacted in the usual way. In this manner 122.1 g of crude O- and C-alkylates (85.2:5.2) were obtained. The crude product was heated at 155°–170° C. for 4.5 hours affording 116.6 g of crude aldehyde. This material was distilled to afford 87 g of purified product (67% yield). BP 50° C./0.03 mmHg; $^1$H-NMR (300 MHz), δ0.88 (9H, s), 0.91 (3H, s), 0.92 (1H, m), 0.98 (3H, d, J=6.6 Hz), 1.16, (1H, m), 1.64 (3H, s), 1.78 (1H, m), 2.18 (1H$_A$, A part of AB quartet, J$_{AB}$=14.0 Hz), 2.43 (1H$_B$, B part of AB quartet, J$_{AB}$=13.7 Hz), 4.67 (1H, s), 4.82 (1H, s), 9.52 (1H, s); $^{13}$C-NMR (75 MHz), δ14.05, 17.36, 18.84, 24.94, 30.58, 34.07, 43.54, 46.89, 54.12, 115.69, 142.24, 208.19; IR (Neat), 2960, 2700, 1730, 1645, 1470, 1370, 890 cm$^{-1}$; MS (m/e), 210 (M$^+$), 195, 177, 154, 139, 126, 112, 97, 83 (Base);

Odor: Fruity weak

Example 74

2-Methyl-2-(4,4-dimethylpent-2-yl)-4-pentenal (mixture of diastereomers)

In a similar manner to Example 6, 100 g of the aldehyde from Example 72 at a purity of 96% (0.61 mole) in 50 ml of DMF, 80 g of potassium t-butoxide (0.68 mole) in 500 ml of DMF, and 53 g of allyl chloride (0.69 mole) in 50 ml of DMF were reacted in the usual manner. In this way 90.5 g of crude O- and C-alkylates (65.7:9.6) and 12.2% of starting material were produced. The crude product was heated at 155°–170° C. for 3 hours to afford 87 g of crude aldehyde. This material was distilled to afford 51 g of purified product (43% yield). BP 45° C./0.15 mmHg; $^1$H-NMR (300 MHz), δ0.89 (9H, s), 0.93 (3H, s), 0.94 (1H, m), 0.98 (3H, d, J=6.84 Hz), 1.2 (1H, m), 1.84 (1H, m), 2.18 (1H, m), 2.35 (1H, m), 5.06 (2H, m), 5.67 (1H, m), 9.45 (1H, s); $^{13}$C-NMR (75 MHz), δ13.99, 16.69, 18.15, 30.03, 32.54, 38.98, 46.38, 53.29, 118.23, 133.47, 207.26; IR (Neat), 2960, 2700, 1730, 1640, 1480, 1370, 920 cm$^{-1}$; MS (m/e), 181 (M$^+$-15), 98, 83, 69, 57 (Base);

Odor: Fruity

Example 75

2,4-Dimethyl-2-(4,4-dimethylpent-2-yl)4-pentenol (mixture of diastereomers)

Similar to Example 7, 60 g of the aldehyde from Example 73 at a purity of 97.4% (0.278 mole), 125 ml of isopropanol, and 33 g of aluminum isopropoxide (0.153 mole) were refluxed for 1 hour. The usual work-up afforded 59.5 g of crude alcohol. The crude alcohol was distilled to afford 52.6 g of purified product (89% yield). BP 73° C./0.04 mmHg; $^1$H-NMR (300 MHz), δ0.86 (3H, s), 0.91 (9H, s), 0.93 (3H, d, J=6.6 Hz), 1.4–1.72 (3H, m), 1.82 (3H, s), 1.90–2.15 (2H, m), 3.48 (2H, m), 4.73 (1H, s), 4.85 (1H, s), hydroxyl proton exchanges out; $^{13}$C-NMR (75 MHz), δ17.24, 17.78, 19.17, 25.42, 30.22, 33.94, 41.66, 42.20, 45.48, 67.94, 114.37, 144.67; IR (Neat), 3400, 2960, 1640, 1470, 1370, 1035, 890 cm$^{-1}$; MS (m/e), 197 (M$^+$-15), 181, 156, 137, 123, 109, 95, 83, 69, 57 (Base);

Odor: Weak

Example 76

2-Methyl-2-(4,4-dimethylpent-2-y)-4-pentenol (mixture of diastereomers)

Similar to Example 7, 30 g of the aldehyde from Example 74 at a purity of 96.5% (0.147 mole), 125 ml of isopropanol, and 17 g of aluminum isopropoxide (0.083 mole) were refluxed for 1 hour. The usual work-up afforded 29.9 g of crude alcohol. The crude alcohol was distilled to afford 27.8 g of purified product (95% yield). BP 62° C./0.12 mmHg; $^1$H-NMR (300 MHz), δ0.73–0.93 (7H, m), 0.90 (9H, s), 1.37–1.65 (3H, m), 2.09 (2H, m), 3.44 (2H, m), 5.06 (2H, m), 5.86 (1H, m); $^{13}$C-NMR (75 MHz), δ17.13, 18.04, 30.23, 31.07, 32.72, 39.85, 40.97, 45.41, 67.84, 116.94, 135.94; IR (Neat), 3360, 2980, 1640, 1470, 1370, 1040, 1025, 910 cm$^{-1}$; MS (m/e), 183 (M$^+$-15), 157, 83, 69, 57 (Base);

Odor: Weak

Example 77

2,2,4-Trimethyl-4-(4,4-dimethylpent-2-yl)tetrahydrofuran. (mixture of diastereomers)

Similar to Example 4, 46.1 g of the alcohol from Example 75 at a purity of 98.3% (0.213 mole), 1.0 g of Amberlyst-15, and 150 ml of heptane were refluxed for 1 hour. After the usual work-up 47 g of crude tetrahydrofuran was obtained. The crude product was distilled to afford 44.3 g of purified product (98% yield). BP 43° C./0.15 mmHg; $^1$H-NMR (300 MHz), δ0.90 (9H, s), 0.93 (3H, d, J=6.69 Hz), 0.9–1.25 (2H, m), 1.02 (3H, s), 1.22 (3H, s), 1.30 (3H, s), 1.56 (3H, m), 3.54 (2H, m); $^{13}$C-NMR (75 MHz), δ18.97, 20.55, 28.99, 29.77, 29.86, 30.23, 37.87, 47.73, 48.97, 52.15, 77.68, 80.84; IR (Neat), 2980, 1480, 1370, 1060 cm$^{-1}$; MS (m/e), 197 (M$^+$-15), 123, 83, 69, 57, 43 (Base);

Odor: Decatone musty

Example 78

2,4-Dimethyl-4-(4,4-dimethylpent-2-yl)tetrahydrofuran (mixture of diastereomers)

Similar to Example 4, 22.5 g of the alcohol from Example 76 at a purity of 98.3% (0.11 mole), 0.6 g of Amberlyst-15, and 100 ml of heptane were refluxed for 12 hours. After the usual work-up 23.2 g of crude tetrahydrofuran were obtained. The crude tetrahydrofuran was distilled to afford 19.6 g of purified product (89% yield). BP 34° C./0.04 mmHg; $^1$H-NMR (300 MHz), spectra consistent with assigned structures; $^{13}$C-NMR (75 MHz), spectra consistent with assigned structures; IR (Neat), 2980, 1480, 1370, 1085, 1070; MS (m/e), 198 (M$^+$), 183, 127, 109, 98, 83, 69, 57, 43 (Base);

Odor: Fresh woody amber clean

Example 79

2-[1-(4-Methyl-3-cyclohexenyl)ethyl]-4-methyl-4-pentenal (mixture of diastereomers)

In a similar manner to Example 6, 171 g of 3-(4-methyl-3-cyclohexen-1-yl)butanal at a purity of 96.2% (0.99 mole) in 100 ml of DMF, 125 g of potassium t-butoxide (1.05 moles) in 600 ml of DMF, and 100 g of methallyl chloride (1.10 moles) in 100 ml of DMF were reacted in the usual way. In this manner 212 g of crude O- and C-alkylates were obtained. The crude product was heated at 165°–170° C. for 10 hours to afford 206.3 g of crude aldehyde. This material was distilled to afford 107 g of purified product (51% yield). BP 91° C./0.15 mmHg; $^1$H-NMR (300 MHz), spectra consistent with assigned structures; $^{13}$C-NMR (75 MHz), δ12.93, 23.34, 25.65, 28.00, 30.56, 30.69, 134.18, 143.24; IR (Neat), 2960, 2705, 1725, 1640, 1450, 1370, 890 cm$^{-1}$; MS (m/e), 220 (M$^+$), 205, 125 (Base), 107, 91, 69;

Odor: Fruity leafy green

Example 80

2-[1-(4-Methyl-3-cyclohexenyl)ethyl]-4-methyl-4-pentenol (mixture of diastereomers)

Similar to Example 2, 90.2 g of the aldehyde from Example 79 at a purity of 94% (0.385 mole), 7.5 g of sodium borohydride (0.198 mole) in 250 ml of ethanol were reacted in the usual manner. After the usual work-up 90.3 g of crude alcohol was obtained. This material was distilled to afford 26.7 g of cyclized tetrahydrofuran (see Example 81) and 45.8 g of desired alcohol (54% yield). BP 106° C./0.2 mmHg; $^1$H-NMR (300 MHz), spectra consistent with assigned structures; $^{13}$C-NMR (75 MHz), δ11.55, 22.09, 23.39, 26.51, 27.92, 29.00, 30.90, 36.08, 37.32, 39.49, 64.97, 111.70, 120.79, 134.00, 145.53; IR (Neat), 3330, 2960, 1650, 1450, 1380, 1040, 890 cm$^{-1}$; MS (m/e), 222 (M$^+$), 207, 189, 147, 133, 121 (Base), 107, 93, 81, 67, 55, 41;

Odor: Weak

Example 81

2,2-Dimethyl-4-[1-(4-methyl-3-cyclohexen-1-yl)-ethyl]tetrahydrofuran (mixture of diastereomers)

Similar to Example 3, 70.0 g of the alcohol from Example 80 at a purity of 81% (0.255 mole), 0.35 g of p-TSA and 275 ml of hexane were refluxed for 20 hours. After the usual work-up 70 g of crude tetrahydrofuran were obtained. The crude material was distilled to afford 54 g of purified product (95% yield). BP 79° C./0.07 mmHg; $^1$H-NMR (300 MHz), δ0.78 (3H, m), 1.20 (3H, s), 1.29 (3H, s), 1.2–2.1 (10H, m), 1.63 (3H, s), 2.40 (1H, m), 3.44 (1H, m), 3.98 (1H, m), 5.38 (1H, br s); $^{13}$C-NMR (75 MHz), δ13.98, 23.96, 25.98, 28.93, 29.40, 31.46, 31.53, 37.41, 41.48, 43.90, 44.69, 72.30, 81.11, 121.34, 134.45; IR (Neat), 2980, 1455, 1365, 1055 cm$^{-1}$; MS (m/e), 222 (M$^+$), 207, 204, 189, 147, 125, 121, 107, 95, 81, 67, 55 (Base);

Odor: Green rosey weak

Example 82

2,2-Dimethyl-4-[1-(4-methylcyclohex-1-yl)ethyl]-tetrahydrofuran (mixture of diastereomers)

Similar to Example 9, 35.7 g of the tetrahydrofuran from Example 81 at a purity of 97.2% (0.156 mole) were hydrogenated on a Parr shaker at 25°–30° C. in 50 ml of ethanol using 0.75 g of 5% Pd on carbon. After the usual work-up 36.6 g of crude product were obtained. The material was distilled to afford 34.4 g of purified tetrahydrofuran (98% yield). BP 75° C./0.10 mmHg; $^1$H-NMR (300 MHz), spectra consistent with assigned structures; $^{13}$C-NMR (75 MHz), spectra consistent with assigned structures; IR (Neat), 2965, 1450, 1370, 1055 cm$^{-1}$; MS (m/e), 223 (M$^+$-1), 209, 191, 151, 135, 123, 109, 95, 81, 69, 55 (Base);

Odor: Bell pepper green

Example 83

2-(2-Methyl-2-propenyl)-3,7,7-trimethylbicyclo[4.1.0]-heptane-2-carboxaldehyde (mixture of diastereomers)

A 4 neck 2 liter round bottomed flask was charged with 500 ml of DMF and 78.0 g of potassium t-butoxide (0.66 mole). The flask was cooled to 0° C. and 100.0 g of 2-formylcarane at a purity of 75% (0.45 mole) in 75 ml of DMF were added dropwise over 30 minutes at 0°–5° C. The mixture was stirred for 20 minutes at 0°–5° C. Then 60.0 g of methallyl chloride (0.66 mole) in 50 ml of DMF were added dropwise over about 25 minutes between 5°–12° C. The batch was poured with stirring into 2 liters of cold brine and extracted with 3×250 ml of hexane. The hexane extracts were washed with 3×500 ml of water and 500 ml of brine. The hexane was dried with sodium sulfate, filtered, and concentrated in vacuo. In this way 127.8 g of crude product were obtained. The crude product was charged into a 250 ml 3 neck flask and heated under nitrogen at 165°–180° C. for 4.5 hours. The crude aldehyde was distilled to afford 88.4 g of purified product (80% yield). BP 79° C./0.1 mmHg; $^1$H-NMR (300 MHz), δ0.6–1.0 (3H, m), 1.04 (3H, s), 1.06 (3H, s), 1.0–1.12 (2H, m), 1.2–1.4 (3H, m), 1.6–1.8 (2H, m), 1.82 (3H, s), 2.44 (2H, m), 4.83 (2H, m), 9.63 (1H, s); $^{13}$C-NMR (75 MHz), δ16.44, 17.68, 20.06, 20.31, 24.66, 27.04, 28.76, 31.24, 33.36, 40.74, 45.73, 49.66, 115.93, 141.89, 204.41; IR (Neat), 2970, 2730, 1725, 1645, 1460, 1380, 895 cm$^{-1}$; MS (m/e), 220 (M$^+$), 205, 191, 177, 165, 147, 135, 121,107, 93, 81, 69, 55, 41 (Base);

Odor: Camphoraceous

Example 84

2-(2-Methyl-2-propenyl)-3,7,7-trimethylbicyclo[4.1.0]-hept-2-yl methanol (mixture of diastereomers)

A 500 ml 4 neck flask was charged with 125 ml of dry isopropanol and 32 g of aluminum isopropoxide (0.148 mole). The contents of the flask were brought to reflux and then 60.0 g of the aldehyde from Example 83 at a purity of 93.8% (0.255 mole) were added dropwise over 45 minutes. The reaction was refluxed for 1 hour. After cooling a Dean-Stark trap was placed on the flask and 128 ml of isopropanol/acetone were distilled out to a pot temperature of 107° C. After cooling to room temperature, the batch was extracted with 200 ml of 10% sulfuric acid and 200 ml of hexane. The hexane was washed with 50 ml of water, 50 ml of 5% sodium carbonate, and 50 ml of brine. The hexane extract was dried with magnesium sulfate, filtered, and concentrated in vacuo to yield 60.6 g of crude product which was distilled from 1 g of soda ash to yield 54.4 g of purified alcohol (89% yield). BP 88° C./0.09 mmHg; $^1$H-NMR (300 MHz), $\delta$0.58 (1H, m), 0.76 (3H, d, J=6.81 Hz), 0.97 (2H, m), 1.06 (3H, s), 1.14 (2H, m), 1.26 (3H, s), 1.50 (1H, m), 1.75–1.9 (2H, m), 1.84 (3H, s), 2.1–2.6 (2H, m), 3.25–3.7 (2H, m), 4.81 (1H, s), 4.87 (1H, s); $^{13}$C-NMR (75 MHz), spectra consistent with assigned structures; IR (Neat), 3450, 2970, 1640, 1460, 1375, 1040, 890 cm$^{-1}$; MS (m/e), 222 (M$^+$), 207, 191, 167, 149, 135, 121, 107, 93, 81, 69, 55, 41 (Base);

Odor: Woody

Example 85

6,8-Methano-3,3,7,7,11-pentamethyl-2-oxaspiro[4.5]-decane (mixture of diastereomers)

A 3 neck 1 liter flask was charged with 218 g of the alcohol from Example 84 at a purity of 89% (0.87 mole), 500 ml of hexane, and 2.5 g of p-TSA were refluxed for 24 hours. The batch was cooled and washed with 250 ml of 10% sodium carbonate and then 250 ml of brine. The batch was dried with mangesium sulfate, filtered, and concentrated in vacuo to afford 216 g of crude tetrahydrofuran. The tetrahydrofuran was distilled to afford 186 g of purified product (96% yield). BP 64°–69° C./0.25 mmHg; $^1$H-NMR (300 MHz), spectra consistent with assigned structures; $^{13}$C-NMR (75 MHz), spectra consistent with assigned structures; IR (Neat), 3005, 2980, 1460, 1370, 1065 cm$^{-1}$; MS (m/e), 222 (M$^+$), 207, 192, 177, 166, 149, 135, 121,107, 93, 82, 69, 55, 43 (Base);

Odor: Timberol woody amber

Example 86

3-(2-Methyl-2-propenyl)-2,6,6-trimethylbicyclo[3.1.1]-hept-3-yl methanol (mixture of diastereomers)

In a manner similar to Example 42, 6.89 g of 2,6,6-trimethyl-3-(2-methyl-2propenyl)bicyclo[3.1.1]hept-3-yl carboxaldehyde at a purity of 95.3% (0.03 mole), 0.56 g of lithium aluminum hydride (0.014 mole), and 50 ml of ether were reacted in the usual way to obtain 6.7 g of crude alcohol (100% yield); $^1$H-NMR (300 MHz), $\delta$0.99 (3H, s), 1.04 (3H, d, J=7.89 Hz), 1.21 (3H, s), 1.41 (1H, m), 1.89 (3H, s), 1.78–1.97 (4H, m), 2.1–2.6 (4H, m), 3.5–3.85 (2H, m), 4.85 (1H, s), 4.93 (1H, s), OH proton exchanges out; $^{13}$C-NMR (75 MHz), $\delta$17.09, 19.36, 23.50, 25.67, 28.39, 29.07, 35.77, 37.41, 39.24, 42.34, 50.54, 54.03, 67.76, 115.78, 145.32; IR (Neat), 3400, 2950, 1640, 1460, 1370, 1020, 890 cm$^{-1}$; MS (m/e), 207 (M$^+$-15), 191, 166, 149, 135, 121, 107, 93 (Base), 83, 79, 69, 55, 41.

Example 87

7,9-Methano-3,3,6,8,8-pentamethyl-2-oxaspiro[4.5]-decane (mixture of diastereomers)

Similar to Example 4, 6.3 g of the crude alcohol from Example 86 at a purity of 95.6%, 0.75 g of Amberlyst-15, and 65 ml of hexane were refluxed for 24 hours. After the usual work-up 5.8 g of crude tetrahydrofuran was obtained. The crude was distilled to afford 4.4 g of purified product (73% yield). BP 59° C./0.09 mmHg; $^1$H-NMR (300 MHz), $\delta$0.89 (3H, s), 1.12 (3H, d, J=7.68 Hz), 1.19 (3H, s), 1.21 (1H, m), 1.26 (3H, s), 1.29 (3H, s), 1.86–2.05 (6H, m), 2.15–2.25 (2H, m), 3.54 (1H$_B$, B part of AB quartet, J=8.8 Hz), 4.02 (1H$_A$, A part of AB quartet, J=8.8 Hz); $^{13}$C-NMR (75 MHz), $\delta$17.52, 23.16, 28.09, 29.55, 29.95, 30.24, 38.41, 41.20, 41.47, 43.07, 46.22, 48.98, 65.31, 76.30, 80.57; IR (Neat), 2970, 1455, 1370, 1070, 1045 cm$^{-1}$; MS (m/e), 222 (M$^+$), 207, 192, 180, 166, 149, 135, 121, 107, 93, 69, 55, 43 (Base);

Odor: Woody amber camphoraceous

Example 88

1-(2-Methyl-2-property)-3-(1,1-dimethylethyDcyclo-hexane-1-carboxaldehyde (mixture of diastereomers)

Similar to Example 6, 17.0 g of 3-(1,1-dimethylethyl)cyclohexane carboxaldehyde (prepared by the method of E. Heilweil and J. Virgilio, Organic Preparations and Procedures, 14 (1–2), 9 (1982) at a purity of 87% (0.088 mole) in 20 ml of DMF, 11.9 g of potassium t-butoxide (0.10 mole) in 60 ml of DMF, and 12.0 g of methallyl chloride (0.13 mole) in 10 ml of DMF were reacted in the usual manner. The resulting mixture of O- and C-alkylates, 21.6 g, was heated at 155° C. for 1 hour. The crude aldehyde so obtained, 19 g, was distilled to afford 8.7 g of purified product (45% yield). BP 57° C./0.1 mmHg; $^1$H-NMR (300 MHz), $\delta$0.85 (9H, s), 0.97–1.45 (3H, m), 1.66 (3H, s), 1.68–1.74 (3H, m), 2.03–2.40 (5H, m), 4.66 (1H, s), 4.84 (1H, s), 9.50 (1H, s); $^{13}$C-NMR (75 MHz), $\delta$23.26, 24.63, 26.60, 27.34, 31.40, 32.46, 33.79, 44.31, 47.74, 50.56, 115.33, 140.77, 207.33; IR (Neat), 2970, 2690, 1720, 1635, 1450, 1360, 895 cm$^{-1}$; MS (m/e), 222 (M$^+$), 207, 166 (Base), 137, 123, 109, 95, 81, 57, 41.

Example 89

1-(2-Methyl-2-propenyl)-3-(1,1-dimethylethyl)-cyclohexyl methanol (mixture of diastereomers)

Similar to Example 42, 8.19 g of the aldehyde from Example 88 at a purity of 90% (0.033 mole), 0.79 g of lithium aluminum hydride (0.019 mole), and 30 ml of ether were reacted in the usual way to afford 7.63 g of crude alcohol (94% yield). $^1$H-NMR (300 MHz), $\delta$0.84 (9H, s), 0.86–1.4 (5H, m), 1.55–1.8 (5H, m), 1.83 (3H, s), 2.01 (2H, m), 3.58 (2H, s), 4.75 (1H, s), 4.88 (1H, s); $^{13}$C-NMR (75 MHz), $\delta$22.34, 25.62, 27.07, 27.46, 32.39, 33.11, 34.44, 39.26, 42.59, 49.46, 64.89, 114.29, 144.37; IR (Neat), 3380, 2970, 1640, 1480, 1450, 1370, 1045, 890 cm$^{-1}$; MS (m/e), 224 (M⁺), 209, 193, 168, 151, 137, 111, 95, 81, 67, 57 (Base), 41.

Example 90

3,3-Dimethyl-7-(1,1-dimethylethyl)-2-oxaspiro-[4.5]decane (mixture of diastereomers)

Similar to Example 4, 7.03 g of the alcohol from Example 89 at a purity of 92% (0.028 mole), 0.29 g of Amberlyst-15, and 60 ml of heptane were refluxed for 24 hours. The usual work-up afforded 7.2 g of crude tetrahydrofuran. This material was distilled to afford 5.92 g of purified product (92% yield). BP 68° C./0.3 mmHg; $^1$H-NMR (300 MHz), δ0.88 (9H, s), 0.88–1.22 (5H, m), 1.25 (3H, s), 1.26 (3H, s), 1.57 (2H, s), 1.65–1.77 (4H, m), 3.62 (2H$_{AB}$, AB quartet, J$_{AB}$= 8.85 Hz); $^{13}$C-NMR (300 MHz), δ24.31, 26.63, 27.51, 29.02, 29.27, 32.26, 36.92, 39.38, 45.30, 45.53, 54.93, 74.33, 79.49; IR (Neat), 2960, 1450, 1360, 1050 cm$^{-1}$; MS (m/e), 224 (M⁺), 223 (Base), 165, 123, 109, 95, 81, 67, 57, 43;

Odor: Dry woody earthy

Example 91

The compound of Example 85 was odor evaluated neat and found to possess a strong, predominantly dry, woody, ambery odor.

Separately, it was incorporated into a simple perfume composition at a 7.5% level, with the following effect. The perfume composition without the compound of Example 85 had a woody, musky, powdery odor. When the compound of Example 85 was added, it gave strength and sophistication, imparting a dry, ambery odor throughout the composition.

| Ingredient | A | B |
|---|---|---|
| BENZYL SALICYLATE | 18.70 | 18.70 |
| ISO EUGENOL HT | 3.11 | 3.11 |
| LACTONE MC-15/ PENTADACANOLIDE | 1.91 | 1.91 |
| LYRAL | 20.50 | 20.50 |
| METHYL CEDRYL KETONE PRIME/VERTOFIX CR | 27.74 | 27.74 |
| MUSK KETONE | 11.20 | 11.20 |
| SANDELA/SANTALEX | 9.34 | 9.34 |
| COMPOUND OF EXAMPLE 85 | -0- | 7.50 |
| | 92.50 | 100.00 |

Example 92

The compound of Example 56, which exhibits a strong, wood amber odor with a dry and powdery feel, was evaluated in the formulations shown below. When used at a level of 10% in a masculine fragrance, it created a warm woody middle note with a slight powdery feel. This chemical can also be used in higher concentration along side citrus, herbaceous and oriental accords. It also, blended well with a floral fruity composition where it functioned as a support next to Methyl Ionones.

| Masculine Composition | | |
|---|---|---|
| Item | A | B |
| Armoise Off Maroc Decolorized | 10 | 10 |
| Bergamot 131/2/1C | 100 | 100 |
| Bergamot Oil Zest Extra | 100 | 100 |
| Clove Bud Oil | 12 | 12 |

| Masculine Composition | | |
|---|---|---|
| Item | A | B |
| Coumarin | 10 | 10 |
| Dimetol | 5 | 5 |
| Dipropylene Glycol/DPG | 263 | 263 |
| Galbanum Coeur @ 10% DPG | 30 | 30 |
| Hedione | 70 | 70 |
| Hydrocarboresin SB | 5 | 5 |
| Iso Butyl Quinoline @ 10% DPG | 20 | 20 |
| Iso Propyl Quinoline @ 1% DPG | 25 | 25 |
| Labdanum Res Brut H @ 50% DPG | 40 | 40 |
| Lemon Oil California Distilled | 100 | 100 |
| Patchouly Oil Rustless Light | 65 | 65 |
| Petitgrain Oil SA Pure | 2 | 2 |
| Reseda Body @ 10% DPG | 5 | 5 |
| Styralyl Acetate | 10 | 10 |
| Tarragon Oil Extra/Estragon Oil | 11 | 11 |
| Thyme Absolute Spanish | 5 | 5 |
| Triplal @ 10% DPG | 12 | 12 |
| Compound of Example 56 | -0- | 100 |
| | 900 | 1,000 |

| Floral Composition | | |
|---|---|---|
| Item | A | B |
| Aldehyde C-10 @ 1% DPG | 45 | 45 |
| Aldehyde C-14 | 90 | 90 |
| Allyl Amyl Glycolate @ 10% DPG | 60 | 60 |
| Allyl Cyclo Hexyl Propionate @ 1% DPG | 9 | 9 |
| Amyl Acetate 95/100% IS STD @ 1% DPG | 60 | 60 |
| Benzyl Acetate Extra | 30 | 30 |
| Calone 1951 @ 10% DPG | 45 | 45 |
| Citronellyl Acetate | 30 | 30 |
| Damascenone @ 10% DPG | 3 | 3 |
| Ethyl Butyrate FCC @ 10% DPG | 9 | 9 |
| Galaxolide 50 DEP | 150 | 150 |
| Helional | 30 | 30 |
| Hexenol, Cis-3- @ 1% DPG | 15 | 15 |
| Hexenyl Acetate, Cis-3-/LRG 1241 | 18 | 18 |
| Hexyl Acetate @ 10% DPG | 12 | 12 |
| Laurine Pure | 60 | 60 |
| Lilial | 30 | 30 |
| Methyl Anthranilate | 24 | 24 |
| Phenyl Ethyl Alcohol White Extra | 60 | 60 |
| Tagete Oil Standard @ 10% DPG | 30 | 30 |
| Triplal @ 10% DPG | 90 | 90 |
| Compound of Example 56 | -0- | 100 |
| | 900 | 1,000 |

Example 93

The compound of Example 85, which exhibits a very intense, strong, woody-amber odor, was evaluated in the formulations shown below. When used at a level up to 5% in a masculine fragrance, it enriched the body note and blended well with herbaceous and citrus accords. In a floral composition, it added a sparkling quality due to its intensity.

| Item | A | B |
|---|---|---|
| Masculine Composition | | |
| Armoise Oil Maroc Decolorized | 10 | 10 |
| Bergamot 131/2/1C | 100 | 100 |
| Bergamot Oil Zest Extra | 100 | 100 |
| Clove Bud Oil | 12 | 12 |
| Coumarin | 10 | 10 |
| Dimetol | 5 | 5 |
| Dipropylene Glycol/DPG | 263 | 263 |

| Item | A | B |
| --- | --- | --- |
| Galbanum Coeur @ 10% DPG | 30 | 30 |
| Hedione | 70 | 70 |
| Hydrocarboresin SB | 5 | 5 |
| Iso Butyl Quinoline @ 10% DPG | 20 | 20 |
| Iso Propyl Quinoline @ 1% DPG | 25 | 25 |
| Labdanum Res Brut H @ 50% DPG | 40 | 40 |
| Lemon Oil California Distilled | 100 | 100 |
| Patchouly Oil Rustless Light | 65 | 65 |
| Petitgrain Oil SA Pure | 2 | 2 |
| Reseda Body @ 10% DPG | 5 | 5 |
| Styralyl Acetate | 10 | 10 |
| Tarragon Oil Extra/Estragon Oil | 11 | 11 |
| Thyme Absolute Spanish | 5 | 5 |
| Triplal @ 10% DPG | 12 | 12 |
| Compound of Example 85 | -0- | 100 |
|  | 900 | 1,000 |
| Floral Composition | | |
| Aldehyde C-10 @ 1% DPG | 45 | 45 |
| Aldehyde C-14 | 90 | 90 |
| Allyl Amyl Glycolate @ 10% DPG | 60 | 60 |
| Allyl Cyclo Hexyl Propionate @ 1% DPG | 9 | 9 |
| Amyl Acetate 95/100% IS STD @ 1% DPG | 60 | 60 |
| Benzyl Acetate Extra | 30 | 30 |
| Calone 1951 @ 10% DPG | 45 | 45 |
| Citronellyl Acetate | 30 | 30 |
| Damascenone @ 10% DPG | 3 | 3 |
| Ethyl Butyrate FCC @ 10% DPG | 9 | 9 |
| Galaxolide 50 DEP | 150 | 150 |
| Helional | 30 | 30 |
| Hexenol, Cis-3- @ 1% DPG | 15 | 15 |
| Hexenyl Acetate, Cis-3-/LRG 1241 | 18 | 18 |
| Hexyl Acetate @ 10% DPG | 12 | 12 |
| Laurine Pure | 60 | 60 |
| Lilial | 30 | 30 |
| Methyl Anthranilate | 24 | 24 |
| Phenyl Ethyl Alcohol White Extra | 60 | 60 |
| Tagete Oil Standard @ 10% DPG | 30 | 30 |
| Triplal @ 10% DPG | 90 | 90 |
| Compound of Example 85 | -0- | 100 |
|  | 900 | 1,000 |

Example 94

The compound of Example 8, which exhibits a strong woody amber odor with a green herbal note, was evaluated in the formulations shown below. When used at a level of 10% in a masculine fragrance, it gave a rich warm woody character. This chemical can also be utilized up to 20% in non-floral creations. In floral compositions, lower concentrations of approximately 3–5% give a powerful middle note.

| Item | A | B |
| --- | --- | --- |
| Masculine Composition | | |
| Armoise Oil Maroc Decolorized | 10 | 10 |
| Bergamot 131/2/1C | 100 | 100 |
| Bergamot Oil Zest Extra | 100 | 100 |
| Clove Bud Oil | 12 | 12 |
| Coumarin | 10 | 10 |
| Dimetol | 5 | 5 |
| Dipropylene Glycol/DPG | 263 | 263 |
| Galbanum Coeur @ 10% DPG | 30 | 30 |
| Hedione | 70 | 70 |
| Hydrocarboresin SB | 5 | 5 |
| Iso Butyl Quinoline @ 10% DPG | 20 | 20 |
| Iso Propyl Quinoline @ 1% DPG | 25 | 25 |
| Labdanum Res Brut H @ 50% DPG | 40 | 40 |
| Lemon Oil California Distilled | 100 | 100 |
| Patchouly Oil Rustless Light | 65 | 65 |
| Petitgrain Oil SA Pure | 2 | 2 |
| Reseda Body @ 10% DPG | 5 | 5 |
| Styralyl Acetate | 10 | 10 |
| Tarragon Oil Extra/Estragon Oil | 11 | 11 |
| Thyme Absolute Spanish | 5 | 5 |
| Triplal @ 10% DPG | 12 | 12 |
| Compound of Example 8 | -0- | 100 |
|  | 900 | 1,000 |
| Floral Composition | | |
| Aldehyde C-10 @ 1% DPG | 45 | 45 |
| Aldehyde C-14 | 90 | 90 |
| Allyl Amyl Glycolate @ 10% DPG | 60 | 60 |
| Allyl Cyclo Hexyl Propionate @ 1% DPG | 9 | 9 |
| Amyl Acetate 95/100% IS STD @ 1% DPG | 60 | 60 |
| Benzyl Acetate Extra | 30 | 30 |
| Calone 1951 @ 10% DPG | 45 | 45 |
| Citronellyl Acetate | 30 | 30 |
| Damascenone @ 10% DPG | 3 | 3 |
| Ethyl Butyrate FCC @ 10% DPG | 9 | 9 |
| Galaxolide 50 DEP | 150 | 150 |
| Helional | 30 | 30 |
| Hexenol, Cis-3- @ 1% DPG | 15 | 15 |
| Hexenyl Acetate, Cis-3-/LRG 1241 | 18 | 18 |
| Hexyl Acetate @ 10% DPG | 12 | 12 |
| Laurine Pure | 60 | 60 |
| Lilial | 30 | 30 |
| Methyl Anthranilate | 24 | 24 |
| Phenyl Ethyl Alcohol White Extra | 60 | 60 |
| Tagete Oil Standard @ 10% DPG | 30 | 30 |
| Triplal @ 10% DPG | 90 | 90 |
| Compound of Example 8 | -0- | 100 |
|  | 900 | 1,000 |

Example 95

The compound of Example 56 was evaluated in a woody/sandalwood type accord for toilet soap. The addition of 10% of the compound to the formula enhanced the woody notes, supported the sweet, floral notes and added an amber note, while rounding off the overall character of the fragrance.

| Ingredient | A | B |
| --- | --- | --- |
| ALDEHYDE C-11 UNDECYLENIC | 1.00 | 1.00 |
| AMBROXAN @ 10.0% BB | 3.00 | 3.00 |
| AMYL SAUCYLATE, ISO FCC | 80.00 | 80.00 |
| BENZYL SALICYLATE | 100.00 | 100.00 |
| CEDARWOOD OIL VIRGINIAN BROWN | 40.00 | 40.00 |
| CINNAMIC ALDEHYDE | 7.00 | 7.00 |
| CITRONELLOL AJ | 50.00 | 50.00 |
| COUMARIN | 50.00 | 50.00 |
| DIMETHYL OCTANOL | 3.00 | 3.00 |
| ETHYL VANILLIN | 1.00 | 1.00 |
| EUGENOL | 35.00 | 35.00 |
| EVERNYL/LRG 1201 | 5.00 | 5.00 |
| GALAXOLIDE 50 DEP | 100.00 | 100.00 |
| GERANIOL 600 | 40.00 | 40.00 |
| GERANUM OIL CHINESE | 35.00 | 35.00 |
| HELIOTROPINE | 15.00 | 15.00 |
| IONONE, ALPHA/IRISONE PURE | 15.00 | 15.00 |
| LAVANDIN GROSSO | 35.00 | 35.00 |
| MENTHONE RACEMIC | 5.00 | 5.00 |
| MUSK KETONE | 15.00 | 15.00 |
| MUSK XYLOL | 30.00 | 30.00 |
| PHENYL ETHYL ACETATE | 7.00 | 7.00 |
| PHENYL ETHYL ALCOHOL WHITE EXTRA | 90.00 | 90.00 |
| ROSE CRYSTALS/ROSONE | 8.00 | 8.00 |
| ROSE TW 62/4/1C | 25.00 | 25.00 |
| SANDALORE | 15.00 | 15.00 |
| VERTENEX | 90.00 | 90.00 |

-continued

| Ingredient | A | B |
|---|---|---|
| DIPROPYLENE GLYCOL | 100.00 | 0.00 |
| COMPOUND OF EXAMPLE 56 | -0- | 100.00 |
| | 1000.00 | 1000.00 |

Example 96

The compound of Example 56 was evaluated in a floral/spicy/agrestic formulation, which can be applied to a laundry detergent. The addition of 5% of the compound added depth and gave a woody/amber aspect to the fragrance, while it softened the sharp minty and camphoraceous notes.

| Ingredient | A | B |
|---|---|---|
| ALDEHYDE C-12 LAURIC @ 10.0% DPG | 7.00 | 7.00 |
| AMBROXAN @ 1.0% BB | 2.00 | 2.00 |
| AMYL SALICYLATE, ISO- (EXTRA) | 100.00 | 100.00 |
| ANISIC ALDEHYDE/AUBEPINE | 15.00 | 15.00 |
| AURANTIOL PURE | 15.00 | 15.00 |
| BENZYL SALICYLATE | 100.00 | 100.00 |
| BERGAMOT RN 76/2/1C | 70.00 | 70.00 |
| CINNAMON LEAF OIL BLEACHED/DIST | 7.00 | 7.00 |
| COUMARIN | 5.00 | 5.00 |
| CYCLAPROP | 40.00 | 40.00 |
| DIMETHYL BENZYL CARBINYL ACETATE | 25.00 | 25.00 |
| EUGENOL | 15.00 | 15.00 |
| FIXOLIDE | 40.00 | 40.00 |
| FLEURAMONE | 1.00 | 1.00 |
| GALAXOLIDE 50 DEP | 60.00 | 60.00 |
| GERANIOL 600 | 90.00 | 90.00 |
| HELIOTROPINE | 30.00 | 30.00 |
| HEXYL CINNAMIC ALDEHYDE | 70.00 | 70.00 |
| INDOLE PURE @ 10.0% DPG | 3.00 | 3.00 |
| ISO EUGENOL HT | 5.00 | 5.00 |
| ISORALDEINE 70 | 70.00 | 70.00 |
| PHENYL ETHYL ALCOHOL WHITE EXTRA | 100.00 | 100.00 |
| ROSEMARY OIL SPANISH | 7.00 | 7.00 |
| TERPINEOL, ALPHA/TERPINEOL 900 | 70.00 | 70.00 |
| VIRIDINE | 3.00 | 3.00 |
| DIPROPYLENE GLYCOL | 50.00 | 0.00 |
| COMPOUND OF EXAMPLE 56 | -0- | 50.00 |
| | 1000.00 | 1000.00 |

I claim:

1. A compound selected from the group consisting of a tetrahydrofuran of structure 1

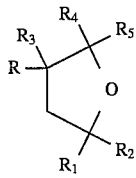

wherein R is a mono-carbocyclic group
where mono-carbocyclic refers to a ring of 5, 7 or 8 carbon atoms, and with at least two methyl groups on the ring, or a bi-carbocyclic group, substituted with at least two methyl groups, and where $R_1=CH_3$, or higher alkyl group, $R_2=H$, $CH_3$, or higher alkyl group, $R_3=H$, or $CH_3$, $R_4$ and $R_5=H$, $CH_3$, or higher alkyl group.

2. The compound of claim 1, which is 2,2,4-trimethyl-4-(2,2,3-trimethyl-3-cyclopenten-1-yl)tetrahydrofuran, including its individual diastereomers and mixtures thereof.

3. The compound of claim 1, which is 2,2-dimethyl-4-(2,2,3-trimethylcyclopentan-1-yl)tetrahydrofuran, including its individual diastereomers and mixtures thereof.

4. The compound of claim 1, which is 2,2-dimethyl-4-(2,3,3-trimethylcyclopentan-1-yl)tetrahydrofuran, including its individual diastereomers and mixtures thereof.

5. The compound of claim 1, which is 2,2-dimethyl-4-(3,3-dimethylbicyclo[2.2.1]heptan-2-yl)tetrahydrofuran, including its individual diastereomers and mixtures thereof.

6. The compound of claim 1, which is 2,4-dimethyl-4-(3,3-dimethylbicyclo[2.2.1]heptan-2-yl)tetrahydrofuran, including its individual diastereomers and mixtures thereof.

7. The compound of claim 1, which is 2,2,4-trimethyl-4-(3,3-dimethylbicyclo[2.2.1]heptan-2-yl)tetrahydrofuran, including its individual diastereomers and mixtures thereof.

8. The compound of claim 1, which is 2,2,5-trimethyl-4-(3,3-dimethylbicyclo[2.2.1]heptan-2-yl)tetrahydrofuran, including its individual diastereomers and mixtures thereof.

9. An odorant composition, characterized by a content of one or more compounds selected from the group consisting of a tetrahydrofuran of structure 1

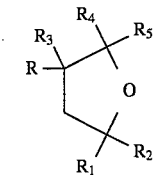

where mono-carbocyclic refers to a ring of 5, 7 or 8 carbon atoms, and with at least two methyl groups on the ring, or a bi-carbocyclic group, substituted with at least two methyl groups, and where $R_1=CH_3$, or higher alkyl group, $R_2=H$, $CH_3$, or higher alkyl group, $R_3=H$, or $CH_3$, $R_4$ and $R_5=H$, $CH_3$, or higher alkyl group.

10. The odorant composition of claim 9, wherein said at least one compound is 2,2,4-trimethyl-4-(2,2,3-trimethyl-3-cyclopenten-1-yl)tetrahydrofuran, including its individual diastereomers and mixtures thereof.

11. The odorant composition of claim 9, wherein said at least one compound is 2,2-dimethyl-4-(2,2,3-trimethylcyclopentan-1-yl)tetrahydrofuran, including its individual diastereomers and mixtures thereof.

12. The odorant composition of claim 9, wherein said at least one compound is 2,2-dimethyl-4-(2,3,3-trimethylcyclopentan-1-yl)tetrahydrofuran, including its individual diastereomers and mixtures thereof.

13. The odorant composition of claim 9, wherein said at least one compound is 2,2-dimethyl-4-(3,3-dimethylbicyclo[2.2.1]heptan-2-yl)tetrahydrofuran, including its individual diastereomers and mixtures thereof.

14. The odorant composition of claim 9, wherein said at least one compound is 2,4-dimethyl-4-(3,3-dimethylbicyclo[2.2.1]heptan-2-yl)tetrahydrofuran, including its individual diastereomers and mixtures thereof.

15. The odorant composition of claim 9, wherein said at least one compound is 2,2,4-trimethyl-4-(3,3-dimethylbicyclo[2.2.1]heptan-2-yl)tetrahydrofuran, including its individual diastereomers and mixtures thereof.

16. The odorant composition of claim 9, wherein said at least one compound is 2,2,5-trimethyl-4-(3,3-dimethylbicyclo[2.2.1]heptan-2-yl)tetrahydrofuran, including its individual diastereomers and mixtures thereof.

* * * * *